(12) United States Patent
Nishide et al.

(10) Patent No.: US 11,453,629 B2
(45) Date of Patent: Sep. 27, 2022

(54) ORGANIC COMPOUND, ORGANIC LIGHT-EMITTING ELEMENT, DISPLAY APPARATUS, IMAGE PICKUP APPARATUS, ELECTRONIC APPARATUS, AND MOVING OBJECT

(71) Applicant: CANON KABUSHIKI KAISHA, Tokyo (JP)

(72) Inventors: Yosuke Nishide, Kawasaki (JP); Naoki Yamada, Inagi (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 374 days.

(21) Appl. No.: 16/572,333

(22) Filed: Sep. 16, 2019

(65) Prior Publication Data

US 2020/0095180 A1  Mar. 26, 2020

(30) Foreign Application Priority Data

Sep. 21, 2018 (JP) .............................. JP2018-177521

(51) Int. Cl.
*C07C 13/62* (2006.01)
*C07C 25/13* (2006.01)
(Continued)

(52) U.S. Cl.
CPC .............. *C07C 13/62* (2013.01); *C07C 25/13* (2013.01); *C07C 255/50* (2013.01);
(Continued)

(58) Field of Classification Search
None
See application file for complete search history.

(56) References Cited

U.S. PATENT DOCUMENTS

2013/0048966 A1* 2/2013 Horiuchi .............. C07D 333/08
257/40

FOREIGN PATENT DOCUMENTS

| EP | 1435669 A2 | 7/2004 |
| JP | 2003-272866 A | 9/2003 |

(Continued)

OTHER PUBLICATIONS

Tamura, "Molecular Design", Ohyobutsuri (Applied Physics), 2000, pp. 1457-1460, vol. 69, No. 12.

*Primary Examiner* — Jay Yang
(74) *Attorney, Agent, or Firm* — Canon U.S.A., Inc., IP Division

(57) ABSTRACT

An organic compound represented by formula (1). In formula (1), each of $R_1$ to $R_{22}$ is independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

(Continued)

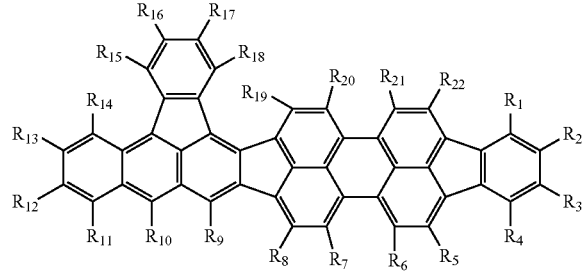

(1)

16 Claims, 8 Drawing Sheets

(51) Int. Cl.
*C07D 217/02* (2006.01)
*C07D 333/76* (2006.01)
*C07C 255/50* (2006.01)
*C07D 307/91* (2006.01)
*H01L 51/00* (2006.01)
*H01L 27/32* (2006.01)
*H01L 51/52* (2006.01)

(52) U.S. Cl.
CPC ......... *C07D 217/02* (2013.01); *C07D 307/91* (2013.01); *C07D 333/76* (2013.01); *H01L 51/0057* (2013.01); *H01L 51/0065* (2013.01); *H01L 51/0067* (2013.01); *H01L 51/0068* (2013.01); *H01L 27/322* (2013.01); *H01L 27/3213* (2013.01); *H01L 51/5206* (2013.01); *H01L 51/5221* (2013.01)

(56) References Cited

FOREIGN PATENT DOCUMENTS

| | | |
|---|---|---|
| JP | 2005-113071 A | 4/2005 |
| JP | 2012-149012 A | 8/2012 |
| JP | 2013-043846 A | 3/2013 |
| WO | 2012/098793 A1 | 7/2012 |

\* cited by examiner

FIG. 1

| STRUCTURAL FORMULA | MOLECULAR WEIGHT OF BASIC SKELETON | SYMMETRY OF BASIC SKELETON | POINT GROUP | SUBLIMABILITY |
|---|---|---|---|---|
| COMPARATIVE COMPOUND 3 | 501 | (TOP) C2 σh | $D_{2h}$ | DECOMPOSED AFTER SUBLIMATION |
| COMPARATIVE COMPOUND 4 | 501 | (TOP) C2 σv (HORIZONTAL) | $C_{2v}$ | NOT DECOMPOSED AFTER SUBLIMATION |
| EXEMPLARY COMPOUND A2 | 575 | (TOP) (HORIZONTAL) 14° | $C_1$ | NOT DECOMPOSED AFTER SUBLIMATION |

FIG. 2

| STRUCTURAL FORMULA | MOLECULAR WEIGHT | DISTANCE FROM MOLECULAR PLANE IN VERTICAL DIRECTION | DECOMPOSITION TEMPERATURE − SUBLIMATION TEMPERATURE |
|---|---|---|---|
| UNSUBSTITUTED COMPOUND (EXEMPLARY COMPOUND A2) | 651 | 2.2Å | 10°C |
| ORTHO-TOLYL COMPOUND (EXEMPLARY COMPOUND B1) | 665 | 3.5Å | 20°C |
| ORTHO-BIPHENYL COMPOUND (EXEMPLARY COMPOUND C1) | 727 | 6.2Å | 40°C |

ORGANIC COMPOUND, ORGANIC LIGHT-EMITTING ELEMENT, DISPLAY APPARATUS, IMAGE PICKUP APPARATUS, ELECTRONIC APPARATUS, AND MOVING OBJECT

BACKGROUND OF THE INVENTION

Field of the Invention

The present disclosure relates to an organic compound, an organic light-emitting element, a display apparatus, an image pickup apparatus, an electronic apparatus, and a moving object.

Description of the Related Art

Organic light-emitting elements (referred to as organic electroluminescent elements or organic EL elements) are electronic elements including a pair of electrodes and an organic compound layer disposed between the electrodes. By injecting electrons and holes through the pair of electrodes, excitons of a luminescent organic compound in the organic compound layer are generated. The organic light-emitting elements emit light when the excitons return to their ground state.

Recent remarkable progress in organic light-emitting elements can achieve low driving voltage, various emission wavelengths, high-speed response, and reductions in the thickness and weight of light-emitting devices.

The standards of sRGB and AdobeRGB have been known as a color reproduction range used for displays, and materials suitable for such a color reproduction range have been demanded. In recent years, the reproduction of BT-2020, which is the standard having a wider color reproduction range, has been demanded.

Compounds having good light-emitting properties have been enthusiastically created to date. Japanese Patent Laid-Open No. 2003-272866 (hereinafter PTL 1) discloses an organic compound represented by structural formula below as an organic compound having good light-emitting properties. This compound is referred to as a compound 1-A in this specification.

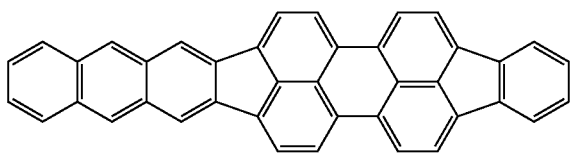

1-A

As a result of studies conducted by the present inventors, the compound 1-A emits red light as described below.

An organic light-emitting element including the organic compound disclosed in PTL 1 is sometimes difficult to reproduce the chromaticity coordinates of red in the color reproduction range of BT-2020. To further extend the color reproduction range, organic compounds that can emit red light at longer wavelengths are required.

SUMMARY OF THE INVENTION

Accordingly, the present disclosure provides an organic compound that can emit red light having a longer wavelength.

An organic compound according to an embodiment of the present disclosure is represented by formula (1) below.

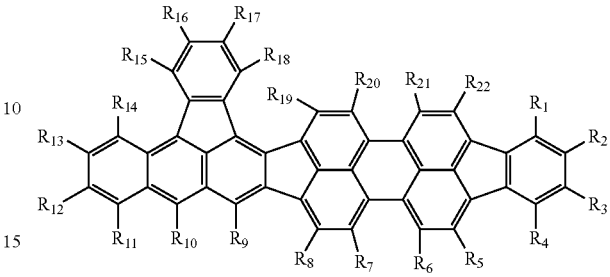

(1)

In the formula (1), each of $R_1$ to $R_{22}$ is independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

Further features of the present disclosure will become apparent from the following description of exemplary embodiments with reference to the attached drawings.

BRIEF DESCRIPTION OF THE DRAWINGS

FIG. 1 illustrates the comparison between an exemplary compound A2, a comparative compound 3, and a comparative compound 4 in terms of symmetry of a molecular structure of a basic skeleton.

FIG. 2 illustrates the state of a phenyl group introduced at a position of $R_9$ in formula (1), the structural formula, and the distance from a molecular plane in a vertical direction.

DESCRIPTION OF THE EMBODIMENTS

Figure 3:
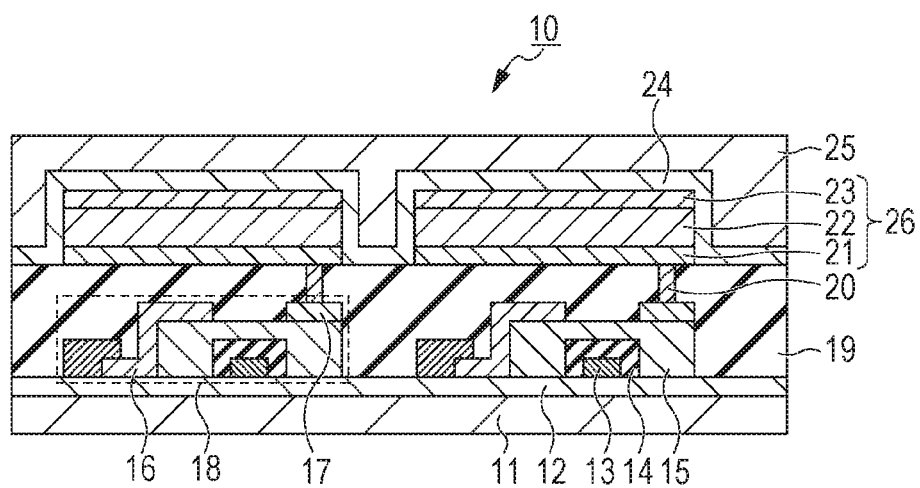
FIG. 3 is a schematic sectional view illustrating an example of a display apparatus including an organic light-emitting element according to an embodiment of the present disclosure and a transistor electrically connected to the organic light-emitting element.

An organic compound according to an embodiment of the present disclosure will be described. The organic compound according to an embodiment of the present disclosure is an organic compound which is represented by formula (1) below and whose basic skeleton itself can emit red light with a high color purity. In this specification, the term "basic skeleton" refers to a structure in which $R_1$ to $R_{22}$ of the compound represented by the formula (1) below each represent a hydrogen atom.

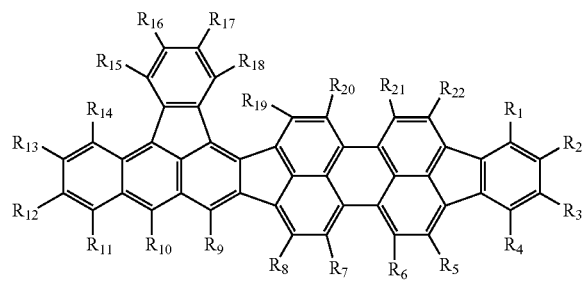

(1)

In the formula (1), each of $R_1$ to $R_{22}$ is independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

In the formula (1), each of $R_1$ to $R_{22}$ may be selected from the group consisting of a hydrogen atom, an alkyl group, and an aryl group.

Non-limiting examples of the halogen atom in the formula (1) include fluorine, chlorine, bromine, and iodine. The halogen atom is preferably a fluorine atom.

The alkyl group in the formula (1) may be an alkyl group having 1 to 10 carbon atoms. Non-limiting specific examples of the alkyl group include a methyl group, an ethyl group, a n-propyl group, an isopropyl group, a n-butyl group, an isobutyl group, a sec-butyl group, a tert-butyl group, an octyl group, a cyclohexyl group, an 1-adamantyl group, and an 2-adamantyl group.

The alkoxy group in the formula (1) may be an alkoxy group having 1 to 10 carbon atoms or an alkoxy group having 1 to 6 carbon atoms. Non-limiting specific examples of the alkoxy group include a methoxy group, an ethoxy group, a propoxy group, an 2-ethyl-octyloxy group, and a benzyloxy group.

The amino group in the formula (1) may be an amino group having an alkyl group, an aryl group, or an aralkyl group as a substituent. Non-limiting specific examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, and an N-piperidyl group. The amino group may be an amino group having no substituent.

The aryl group in the formula (1) may be an aryl group having 6 to 18 carbon atoms. Non-limiting specific examples of the aryl group include a phenyl group, a naphthyl group, an indenyl group, a biphenyl group, a terphenyl group, a fluorenyl group, a phenanthryl group, and a triphenylenyl group.

The heterocyclic group in the formula (1) may be a heterocyclic group having 3 to 15 carbon atoms. The heteroatom in the heterocyclic group may be a nitrogen atom, an oxygen atom, or a sulfur atom. Non-limiting specific examples of the heterocyclic group include a pyridyl group, an oxazolyl group, an oxadiazolyl group, a thiazolyl group, a thiadiazolyl group, a carbazolyl group, an acridinyl group, a phenanthrolyl group, a dibenzofuranyl group, and a dibenzothiophenyl group.

Non-limiting examples of the aryloxy group in the formula (1) include a phenoxy group and a thienyloxy group.

Non-limiting examples of the silyl group in the formula (1) include a trimethylsilyl group and a triphenylsilyl group.

The substituent that may be further included in the alkyl group, the alkoxy group, the amino group, the aryl group, the heterocyclic group, and the aryloxy group may be an alkyl group, an alkoxy group, an aryl group, an aralkyl group, an aryloxy group, a heterocyclic group, a substituted amino group, or a halogen atom. The specific examples of the substituent are those described above. In particular, the substituent may be an alkyl group, an aryl group, or a halogen atom. In the case of a halogen atom, the substituent may be a fluorine atom.

In the case where the basic skeleton of the organic compound according to an embodiment of the present disclosure has a substituent, a compound whose concentration quenching is suppressed, which has an improved sublimability when sublimated, and which has an improved solvent solubility when coated can be obtained.

Next, a method for synthesizing the organic compound represented by the formula (1) will be described. The organic compound represented by the formula (1) can be synthesized with, for example, the following reaction scheme.

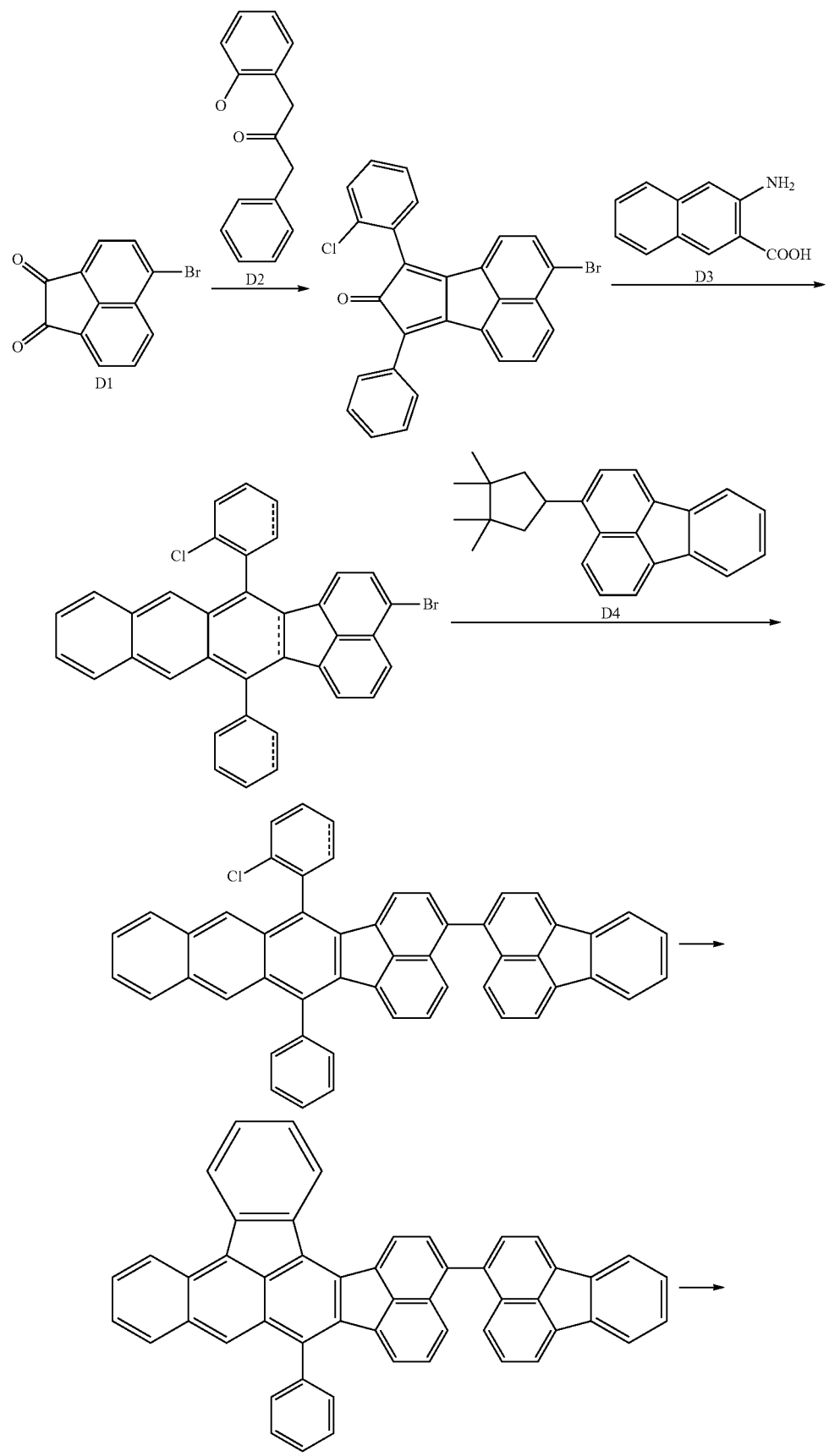

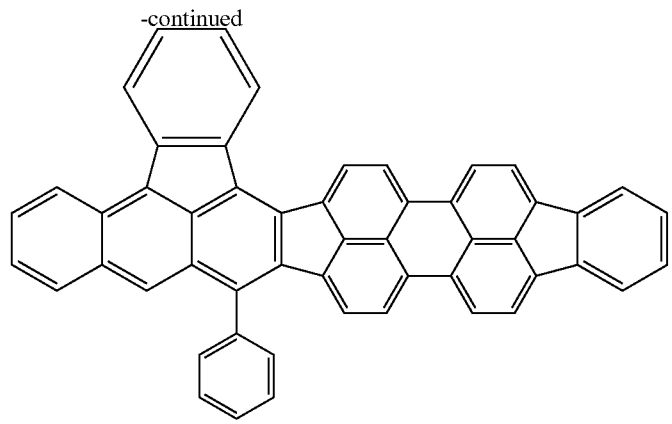

As illustrated in the above synthesis scheme, the organic compound represented by the formula (1) is synthesized using compounds (a) to (d) below as raw materials.
(a) Acenaphthenequinone derivative (D1)
(b) Dibenzyl ketone derivative (D2)
(c) Naphthalene derivative (D3)
(d) Fluoranthene derivative (D4)

Organic compounds with $R_1$ to $R_{22}$ representing desired substituents in the formula (1) can be synthesized by appropriately introducing substituents to the compounds (a) to (d).

In the above synthesis scheme, various organic compounds can be synthesized by changing the derivatives D1 to D4. In each reaction of the synthesis scheme, a catalyst may be used. The catalyst may be a publicly known catalyst such as a palladium catalyst or a phosphoric acid catalyst.

The organic compound represented by the formula (1) is a stable organic compound capable of emitting red light with a high color purity because the organic compound has the following features. Furthermore, the use of this organic compound can provide an organic light-emitting element having high light emission efficiency and high durability.
(1) The emission wavelength of the basic skeleton itself is in a red region with a high color purity.
(2) The HOMO energy is low and the compound itself has high chemical stability.
(3) The compound has an asymmetric structure and thus has low crystallinity.

Hereafter, these features will be described.

In this embodiment, the molecular structure, the Si (singlet excited state) wavelength, the oscillator strength, and the dihedral angle were calculated by using the following molecular orbital calculations.

The density functional theory (DFT), which has been widely used today, was used as a calculation technique of the molecular orbital calculations. The functional was B3LYP and the basis function was 6-31G*. The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010.), which has been widely used today. The basis function may be 6-31G (d).

(1) The Emission Wavelength of the Basic Skeleton Itself is in a Red Region with a High Color Purity In the organic compound represented by the formula (1), the present inventors have focused on the basic skeleton itself. When the light emission generated by the basic skeleton itself is red light having a long wavelength, the color adjustment performed by introducing a substituent can be minimized. If a substituent is introduced to a structure other than the condensed ring structure, the stability may be impaired depending on the substitution position and the types of substituents. In the organic compound represented by the formula (1), the light emission generated by the basic skeleton itself is long-wavelength light emission and thus the wavelength adjustment performed by introducing a substituent is minimized. This leads to high stability of the organic compound itself. In this specification, the long-wavelength red color is also referred to as a red color with a high color purity.

In this embodiment, the desired emission wavelength range is a red region with a high color purity, which is specifically a range of 610 nm or more and 640 nm or less. Herein, the emission wavelength of the organic compound is a maximum peak wavelength in a dilute solution.

Next, the properties of the basic skeleton of the organic compound represented by the formula (1) will be described by comparing the organic compound represented by the formula (1) with a comparative compound. The comparative compound is a comparative compound 1 below. The organic compound represented by the formula (1) is, for example, an exemplary compound A2. Herein, the comparative compound 1 has two phenyl groups. Since the comparative compound 1 has high planarity of the basic skeleton itself, the intermolecular interaction may affect the light emission. To suppress the influence, the phenyl groups are introduced. The comparative compound 1 has phenyl groups and therefore the exemplary compound A2 having a phenyl group is used among exemplary compounds to evaluate the performance under the same conditions.

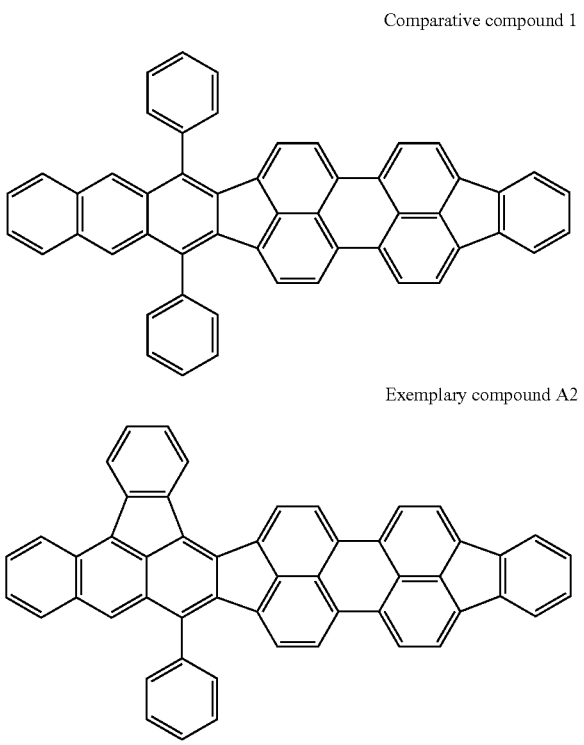

Comparative compound 1

Exemplary compound A2

The exemplary compound A2 is a compound with $R_1$ to $R_8$ and $R_{10}$ to $R_{22}$ representing a hydrogen atom and $R_9$ representing a phenyl group in the formula (1). The exemplary compound A2 is an organic compound having a phenyl group at a position of $R_9$. Therefore, the exemplary compound A2 is not a basic skeleton. However, since the substituent at a position of $R_9$ exerts only a small influence on emission wavelength, the emission wavelength of the exemplary compound A2 can be regarded as the emission wavelength of the basic skeleton itself. For the comparison under the same conditions, an organic compound having a phenyl group at the same position is selected as the comparative compound 1.

The exemplary compound A2 and the comparative compound 1 were compared with each other in terms of maximum peak wavelength. Table 1 below shows the results. The emission wavelength was determined by photoluminescence measurement of a diluted toluene solution at an excitation wavelength of 350 nm at room temperature using an F-4500 manufactured by Hitachi, Ltd.

TABLE 1

| Name of compound | Molecular structure | Actual measurement Maximum peak wavelength/nm |
| --- | --- | --- |
| Comparative compound 1 | 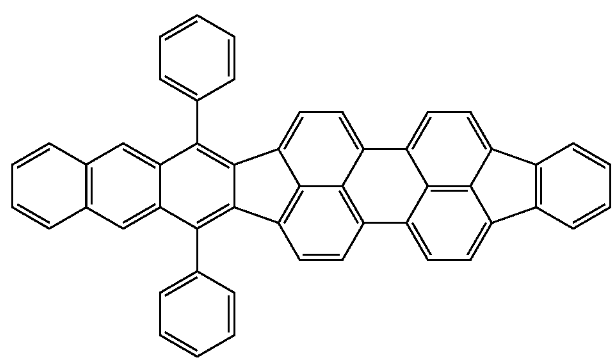 [SMILES: c1ccc(-c2c3c(c(-c4ccccc4)c4cc5ccccc5cc24)-c2ccc4c5ccc6c7c(ccc(c8ccc-3c2c84)c75)-c2ccccc2-6)cc1] | 600 |
| Exemplary compound A2 | 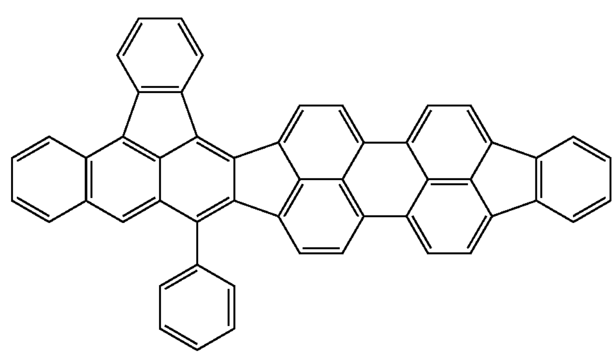 [SMILES: c1ccc(-c2c3cc4ccccc4c4c5ccccc5c(c5c6ccc7c8ccc9c%10c(ccc(c%11ccc(c25)c6c%117)c%108)-c2ccccc2-9)c34)cc1] | 623 |

As is clear from Table 1, the emission color of the comparative compound 1 is red, but is not in the desired wavelength range. In other words, red light with a high color purity is not emitted. In contrast, the exemplary compound A2 has a maximum peak wavelength in the desired range and emits long-wavelength red light. The exemplary compound A2, that is, the basic skeleton of the organic compound represented by the formula (1) emits long-wavelength red light suitable for red in the display standard such as BT-2020.

As described above, the basic skeleton of the organic compound represented by the formula (1) is capable of emitting light with a high color purity. The chromaticity coordinates of red will be described in detail in Examples.

(2) The HOMO Energy is Low and the Compound Itself has High Chemical Stability

In the creation of a material having a desired emission wavelength range, the present inventors have focused on the HOMO energy of molecules. An emission wavelength range on the longer wavelength side means a narrow band gap. To narrow the band gap, the HOMO energy needs to be increased or the LUMO energy needs to be decreased. Herein, high HOMO energy means that the energy level is close to the vacuum level and low HOMO energy means that the energy level is far from the vacuum level. The same applies to the LUMO energy.

Table 2 below shows the molecular orbital calculation values of the Si energy and HOMO energy of the comparative compound 1, a comparative compound 2, and the exemplary compound A2. The Si energy is calculated from the HOMO energy and the LUMO energy and corresponds to a band gap. The comparison of the Si energy allows the comparison of the light emission peak wavelength. The comparison of the HOMO energy allows the comparison of the oxidation potential. The comparison of the LUMO energy allows the comparison of the reduction potential. To achieve long-wavelength light emission and high oxidation resistance, low Si energy and low HOMO energy are desired. The Si energy in Table 2 is an energy on a wavelength basis and therefore the energy decreases as the value increases.

The comparative compound 2 has a structure obtained by fusing a benzene ring to the comparative compound 1 and thus the Si wavelength increases. However, as is clear from Table 2, the HOMO energy of the comparative compound 2 is higher than that of the comparative compound 1. High HOMO energy means low oxidation potential, which indicates low oxidation resistance. That is, the comparative compound 2 has lower oxidation resistance than the comparative compound 1 and the exemplary compound A2. When only conjugation is simply extended as in the comparative compound 2, the HOMO energy tends to increase, which decreases the oxidation resistance.

On the other hand, the organic compound represented by the formula (1) has an emission wavelength in a long-wavelength red region and has lower HOMO energy and lower LUMO energy than the comparative compounds. This is because the molecule is designed so that three electron-attracting five-membered rings are present in the basic skeleton. Therefore, the organic compound represented by the formula (1) has low HOMO energy and low LUMO energy. In other words, the organic compound represented by the formula (1) has high oxidation resistance.

TABLE 2

| Name of compound | Molecular structure | Calculated value | |
| --- | --- | --- | --- |
| | | S1/nm | HOMO/eV |
| Comparative compound 1 | 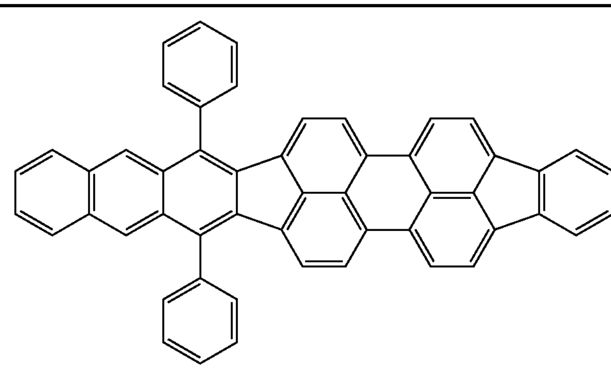 | 582 | −4.76 |
| Comparative compound 2 | 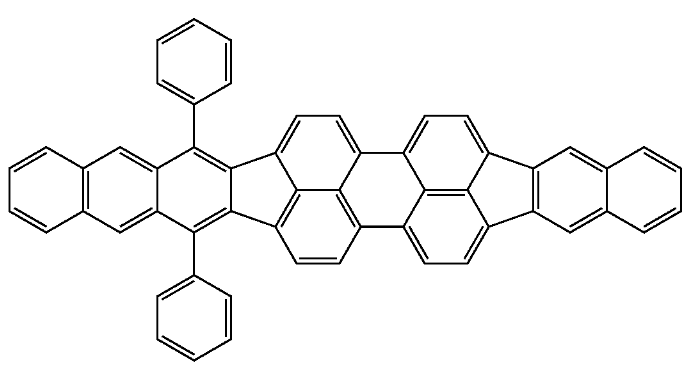 [SMILES: c1ccc(-c2c3c(c(-c4ccccc4)c4cc5ccccc5cc24)-c2ccc4c5ccc6c7c(ccc(c8ccc-3c2c84)c75)-c2cc3ccccc3cc2-6)cc1] | 594 | −4.69 |

TABLE 2-continued

| Name of compound | Molecular structure | Calculated value | |
|---|---|---|---|
| | | S1/nm | HOMO/eV |
| Exemplary compound A2 | 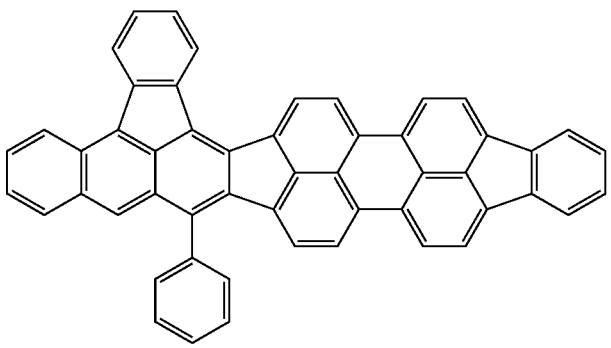 [SMILES: c1ccc(-c2c3cc4ccccc4c4c5ccccc5c(c5c6ccc7c8ccc9c%10c(ccc(c%11ccc(c25)c6c%117)c%108)-c2ccccc2-9)c34)cc1] | 596 | −4.90 |

Table 2 shows that the HOMO energies of the comparative compound 1 and the comparative compound 2 are −4.76 eV and −4.69 eV, respectively. On the other hand, the HOMO energy of the exemplary compound A2 is −4.90 eV, which is lower than those of the comparative compounds. This shows that the exemplary compound A2 is a compound whose emission wavelength is increased, but which is not easily oxidized compared with the comparative compound 1 and the comparative compound 2.

The organic compound represented by the formula (1) has high oxidation resistance and thus an organic light-emitting element that uses such a compound has high stability and high durability.

(3) The Compound has an Asymmetric Structure and Thus has Low Crystallinity

Organic compounds whose basic skeleton itself has a red emission wavelength are compounds having a large conjugation length. Compounds having a large conjugation length tend to have high molecular planarity and thus is easily crystallized because of the intermolecular interaction. When an organic compound is crystallized, the properties of the organic compound itself are undesirably changed. For example, the sublimability is deteriorated and the concentration quenching is caused.

Accordingly, the present inventors have focused on the symmetry of the molecular structure. Molecules having low symmetry are molecules that are not easily crystallized because ordered stacking of molecules is suppressed compared with molecules having high symmetry. Such molecules that are not easily crystallized have high sublimability and the concentration quenching is suppressed. Therefore, the molecular structure may be an asymmetric structure to reduce crystallization.

Herein, high sublimability means that the difference between the sublimation temperature of an organic compound and the thermal decomposition temperature of the organic compound is large and the sublimation temperature is lower than the thermal decomposition temperature. An organic compound having low sublimability may be thermally decomposed during sublimation, which may generate a decomposition product of the organic compound. The decomposition product of the organic compound may exert an undesired influence such as an unexpected reaction. Therefore, the sublimability of the organic compound may be set to be high to suppress the generation of the decomposition product.

In this embodiment, the exemplary compound A2, a comparative compound 3, and a comparative compound 4 were compared with each other in terms of symmetry of the molecular structure of the basic skeleton using a group theory. FIG. 1 illustrates the results. The comparative compound 3 and the comparative compound 4 were used for comparison as examples of the organic compound that has high symmetry and emits red light. In FIG. 1, in the column of "Symmetry of basic skeleton", a phenyl group included in the structural formula is not illustrated because of the comparison of the basic skeleton.

The basic skeleton of the comparative compound 3 has a two-fold rotation axis (C2) in a direction perpendicular to the molecular plane, and also has a two-fold rotation axis (C2) and a symmetry plane ($\sigma_h$) that are orthogonal to the above two-fold rotation axis. Therefore, the point group is classified into $D_{2h}$.

The basic skeleton of the comparative compound 4 has a two-fold rotation axis (C2) in a major-axis direction of the molecular plane, and also has a symmetry plane ($\sigma_v$) including the two-fold rotation axis. Therefore, the point group is classified into $C_{2v}$.

On the other hand, the basic skeleton of the exemplary compound A2 does not have a rotation axis or a symmetry plane ($\sigma$) of the molecular plane. Therefore, the point group is classified into $C_1$. This is because the basic skeleton of the exemplary compound A2 is twisted by about 14° because of the steric repulsion in a molecule.

Therefore, the molecular symmetry is lower in the exemplary compound A2 than in the comparative compound 3 and the comparative compound 4.

As described above, the molecule having low symmetry has low crystallinity and high sublimability. The exemplary compound A2 has a higher molecular weight of the basic skeleton than the comparative compound 3 and the comparative compound 4. Therefore, the exemplary compound A2 is estimated as a compound having a disadvantage in terms of sublimability, but the decomposition has not been observed even after sublimation. The comparative compound 3 has a low molecular weight, but has high symmetry. The sublimation temperature is increased to a temperature close to the decomposition temperature of the organic compound, and therefore the decomposition after sublimation has been observed. The crystallization of the comparative compound 3 seems to be facilitated because of its high symmetry. The decomposition before and after sublimation is determined by whether the purity after sublimation is decreased. The purity was measured by high-performance liquid chromatography using an instrument manufactured by JASCO Corporation.

The exemplary compound A2 has higher sublimability than the comparative compound 4 because the intermolecular distance in a solid state is large due to twisting of the basic skeleton.

Accordingly, the organic compound represented by the formula (1) has a molecular structure having low symmetry and a twisted portion in the basic skeleton. Therefore, the organic compound is a compound having low crystallinity and high sublimability regardless of the basic skeleton having a large conjugation length.

An organic compound that satisfies the following conditions (4) and (5) in addition to the above features (1) to (3) may be used as a compound for the organic light-emitting element. When the conditions (4) and (5) are satisfied, the crystallization is further reduced, which can improve the sublimability and suppress the concentration quenching. The improvement in sublimability can increase the purity of a material through sublimation purification, which makes it easy to produce the organic light-emitting element by vapor deposition. This can decrease the amount of impurities contained in the organic light-emitting element. Thus, a decrease in light emission efficiency due to impurities and a decrease in driving durability can be suppressed. The concentration quenching can also be suppressed from the viewpoint of improving the light emission efficiency of the organic light-emitting element.

(4) The organic compound has a substituent at at least one of $R_9$ and $R_{10}$.

(5) The organic compound has a substituent that covers the basic skeleton.

Hereafter, these conditions will be described.

(4) The Organic Compound has a Substituent at at Least One of $R_9$ and $R_{10}$ In the organic compound represented by the formula (1), a substituent can be introduced to at least one of $R_9$ and $R_{10}$ to suppress intermolecular stacking. Preferably, at least one of $R_9$ and $R_{10}$ has a bulky substituent. By suppressing the intermolecular stacking, the crystallinity can be further reduced. The reduction in crystallinity results in suppression of concentration quenching and improvement in sublimability as described below.

The organic compound represented by the formula (1) has a relatively high planarity. When the organic compound has no substituents, the intermolecular stacking may occur. Therefore, the organic compound may have a substituent at at least one of $R_9$ and $R_{10}$ in the formula (1).

Table 3 shows a dihedral angle between the basic skeleton and a phenyl group introduced to each of $R_1$ to $R_{22}$ in the formula (1). That is, Table 3 shows the degree of twisting between the basic skeleton and the substituent at each of substitution positions. At the substitution positions $R_9$ and $R_{10}$, hydrogen at an ortho position of the phenyl group and hydrogen of the basic skeleton cause a large steric repulsion and thus the dihedral angle is large. Therefore, the planarity on the whole molecule is lost. This effect leads to suppression of intermolecular stacking, reduction in crystallization, suppression of intermolecular concentration quenching, and improvement in sublimability.

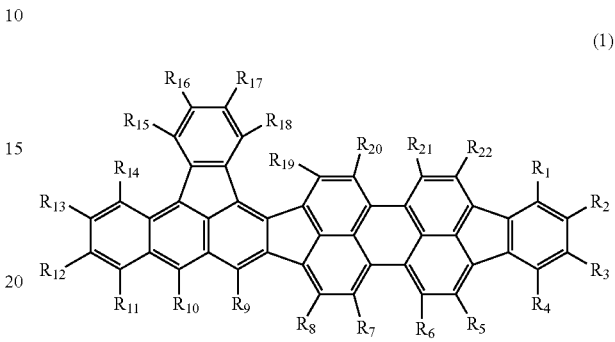

(1)

TABLE 3

| | Substitution position | | | | | | | | | | | | | | |
|---|---|---|---|---|---|---|---|---|---|---|---|---|---|---|---|
| | $R_1$ $R_4$ | $R_2$ $R_3$ | $R_5$ $R_{22}$ | $R_6$ $R_{21}$ | $R_7$ $R_{20}$ | $R_8$ | $R_9$ | $R_{10}$ | $R_{11}$ | $R_{12}$ $R_{13}$ | $R_{14}$ | $R_{15}$ | $R_{16}$ | $R_{17}$ | $R_{18}$ | $R_{19}$ |
| Dihedral angle/° | 59 | 17 | 56 | 68 | 68 | 57 | 90 | 90 | 58 | 17 | 50 | 55 | 38 | 38 | 41 | 42 |

Accordingly, the organic compound preferably has a substituent at at least one of $R_9$ and $R_{10}$, that is, preferably satisfies the condition (4). The substituent introduced is more preferably a bulky substituent. The bulky substituent is a substituent having a large excluded volume.

Such a substituent may be introduced at $R_9$ or $R_{10}$ having a large dihedral angle. Since the crystallization is further reduced as the dihedral angle increases, the $R_9$ and $R_{10}$ produce the largest effect, followed by $R_6$, $R_7$, $R_{20}$, and $R_{21}$. Substitution positions after $R_6$, $R_7$, $R_{20}$, and $R_{21}$ are as shown in Table 3.

(5) The Organic Compound has a Substituent that Covers the Basic Skeleton

To further reduce the crystallization, the present inventors have tried to introduce a substituent that covers the basic skeleton. The substituent that covers the basic skeleton refers to a substituent that covers t-conjugated planes between molecules.

FIG. 2 illustrates the state of a phenyl group introduced at a position of $R_9$ in the formula (1), the structural formula, and the distance from the molecular plane in a vertical direction. FIG. 2 illustrates a compound whose phenyl group has no substituents, an ortho-tolyl compound whose phenyl group has a methyl group at its ortho position, and an ortho-biphenyl compound whose phenyl group has a phenyl group at its ortho position.

It is found that the intermolecular stacking is suppressed as the distance of the substituent that covers the basic skeleton increases from the molecular plane. The phrase "the distance increases from the molecular plane" refers to an increase in distance from the molecular plane in a vertical direction. The phenyl group produces a larger effect of covering the π-conjugated planes than the methyl group and thus the intermolecular stacking can be suppressed.

To reduce the crystallization, the following substituent may be used as the substituent that covers the basic skeleton. In the case of an alkyl group, the substituent is preferably a methyl group, an ethyl group, a propyl group, a butyl group, a hexyl group, or an octyl group and more preferably an isopropyl group or a tert-butyl group that has a large excluded volume.

In the case of an aryl group, the substituent is preferably a phenyl group or a naphthyl group. In particular, the substituent is preferably a phenyl group having a small molecular weight from the viewpoint of sublimability and more preferably a phenyl group having at least one of a methyl group, an isopropyl group, a tert-butyl group, and a phenyl group as a substituent. When the phenyl group has a substituent, the substituent is preferably present at an ortho position.

From this viewpoint, a fluorine atom or a fluorine-substituted aryl group may be introduced.

The substituent may be introduced because when the organic compound contained in a liquid is provided (applied) to a particular position and then the solvent is removed, the properties of the resulting film are improved.

Herein, the exemplary compound A1 and the exemplary compound A2 are compared with each other in terms of the effect of covering by a substituent. The molecular weight is larger in the exemplary compound A2 than the exemplary compound A1, but the difference between the decomposition temperature and the sublimation temperature is larger in the exemplary compound A2 than in the exemplary compound A1. As the difference between the decomposition temperature and the sublimation temperature increases, the temperature margin in sublimation purification increases. Thus, the large temperature difference means high thermal stability. The sublimation temperature is a temperature at which the organic compound is gradually heated at a degree of vacuum of $1 \times 10^{-1}$ Pa in an atmosphere of Ar flow, the sublimation purification is initiated, and the sublimation rate reaches a sufficient sublimation rate. The decomposition temperature is a temperature at which the weight loss determined by TG/DTA measurement reaches 5%.

Accordingly, the organic compound according to an embodiment of the present disclosure has a large difference between the sublimation temperature and the thermal decomposition temperature when the condition (5) is satisfied and thus is a compound having high sublimability.

Since the organic compound represented by the formula (1) has the above properties (1) to (3), the organic compound is an organic compound in which the emission wavelength of the basic skeleton itself is a red color with a high color purity and which has high sublimability. Among the organic compounds represented by the formula (1), the organic compound further having the properties (4) and (5) is an organic compound in which the intermolecular stacking is suppressed and thus the sublimability is improved and the concentration quenching is suppressed.

By using such an organic compound, an organic light-emitting element that has high efficiently and high durability and emits red light with a high color purity can be obtained.

Specific examples of the organic compound according to an embodiment of the present disclosure are shown below. The organic compound according to an embodiment of the present disclosure is not limited thereto.

A1

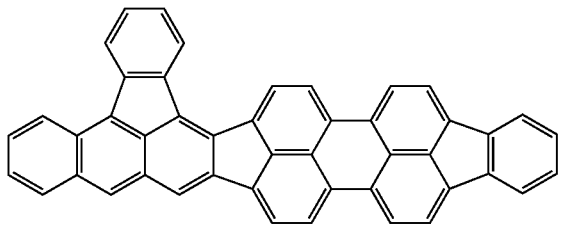

A2

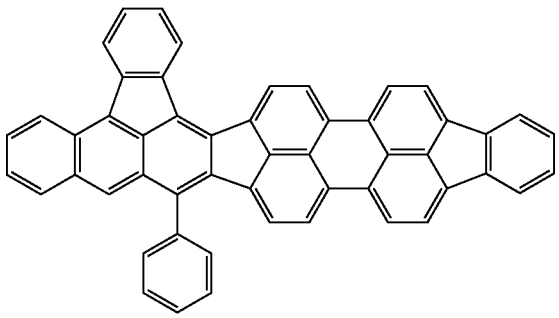

A3

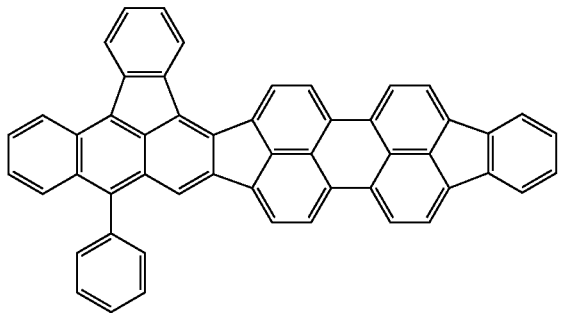

A4

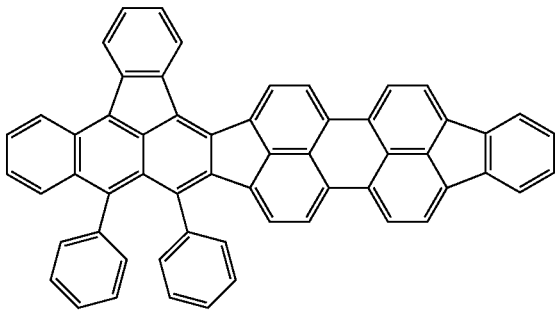

-continued
A5
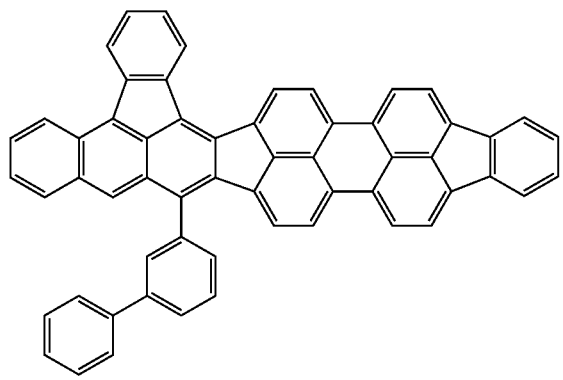
A6
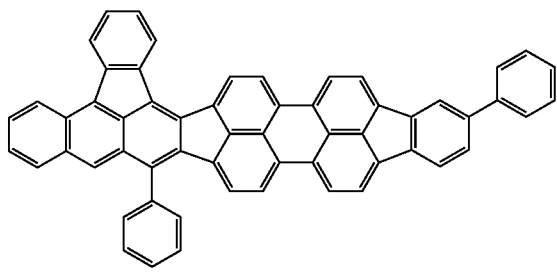
A7
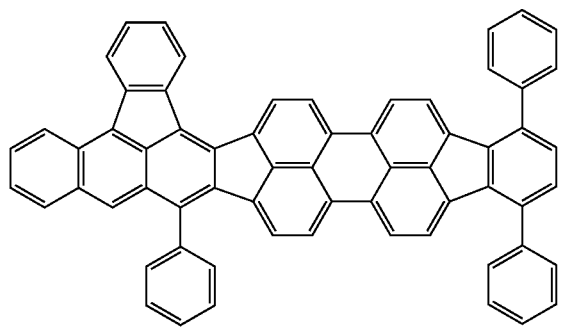
A8
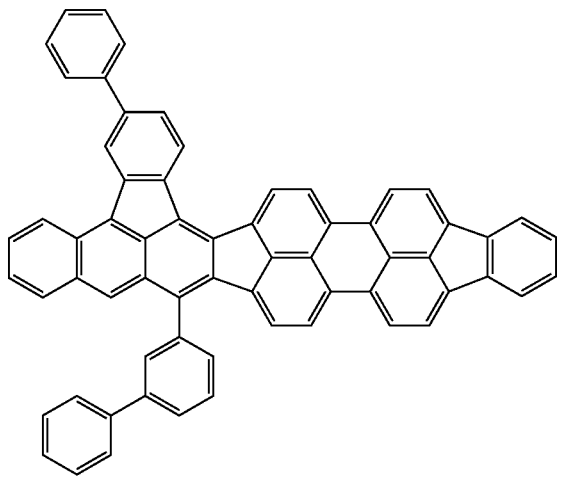
A9
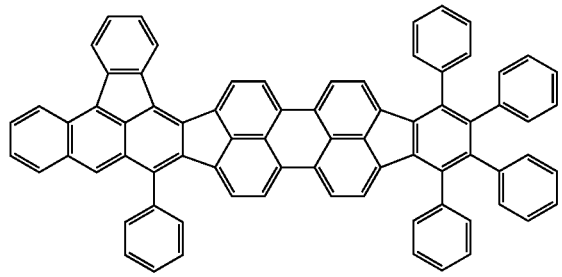
A10
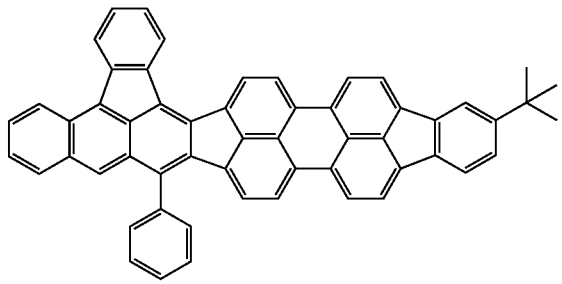
A11
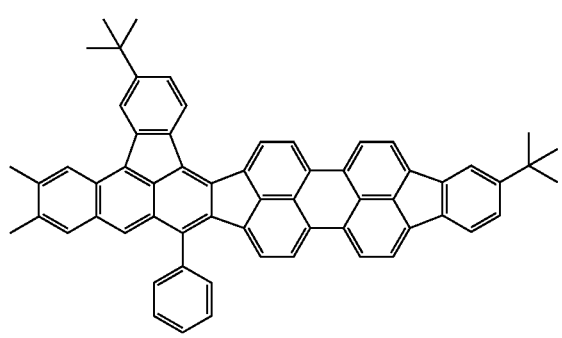

-continued
A12
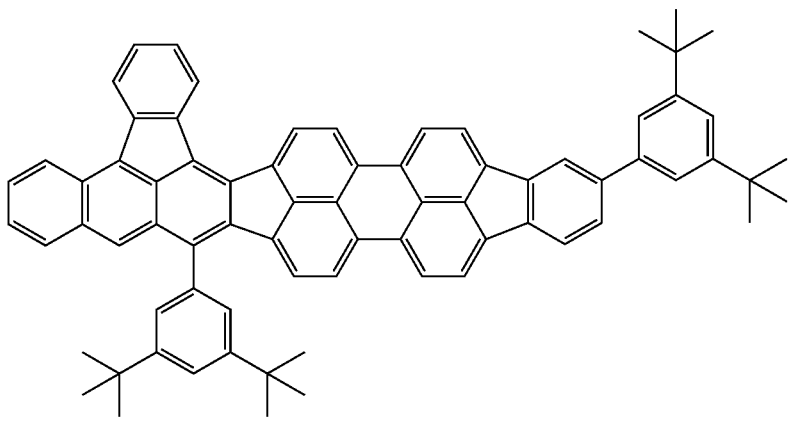
A13
A14
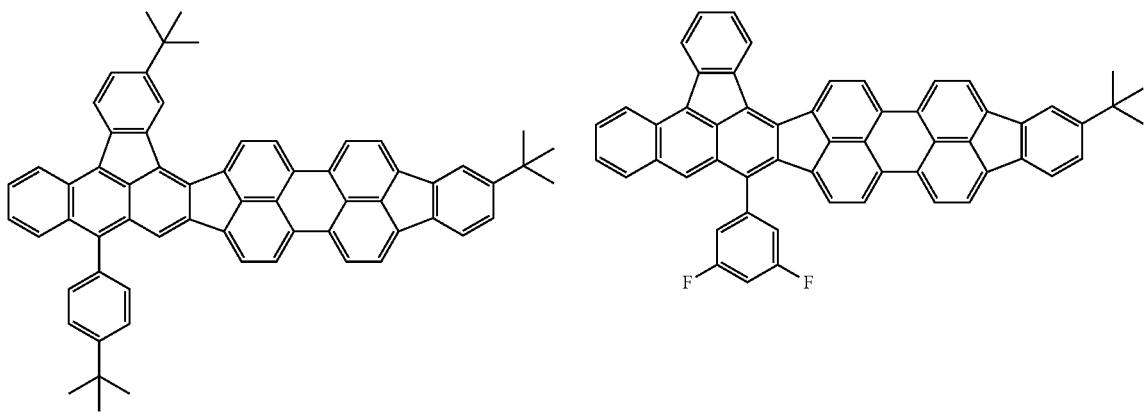
A15
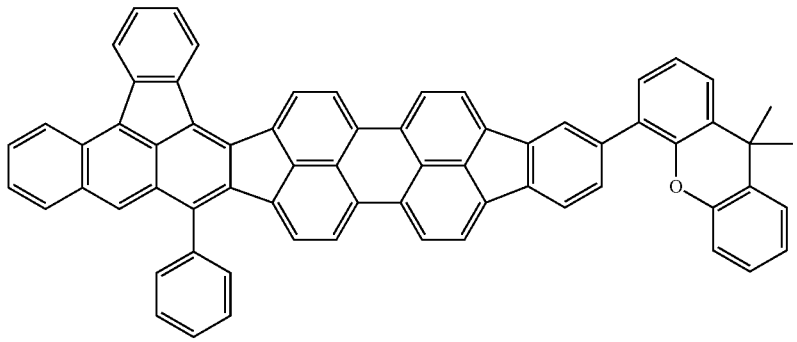
A16
A17
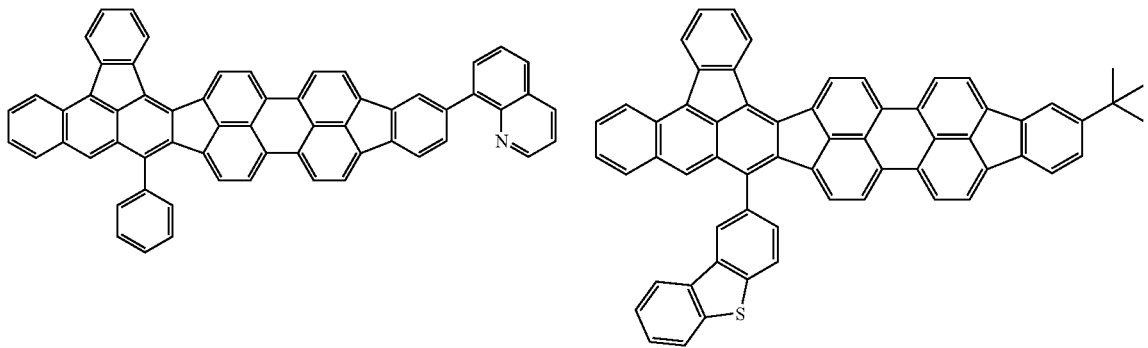

-continued
A18
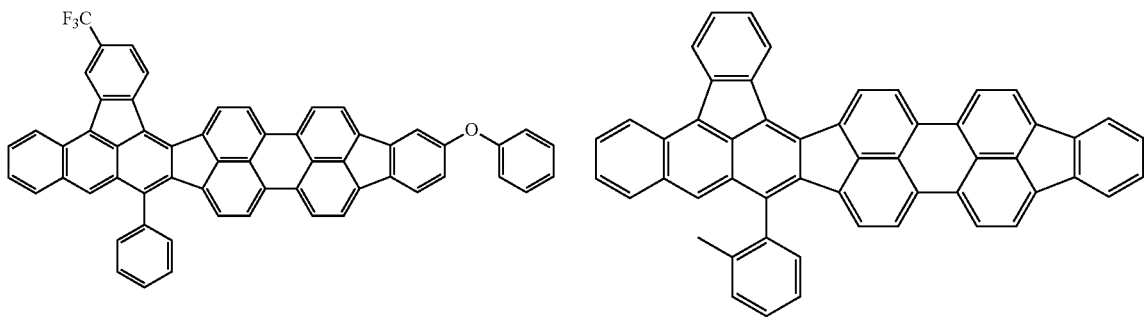
B1
B2 B3
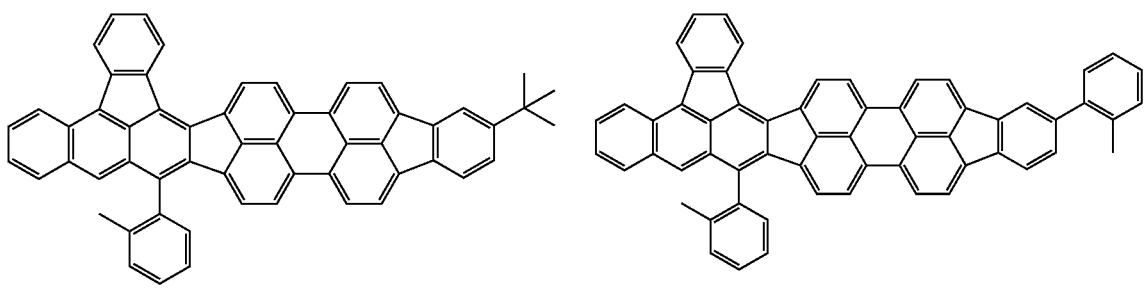
B4
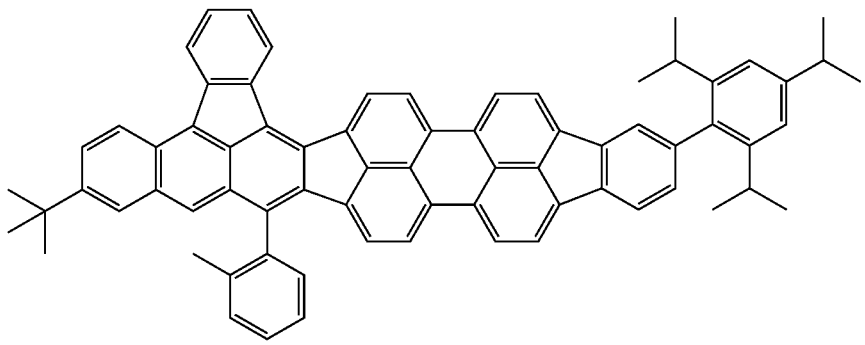
B5 B6
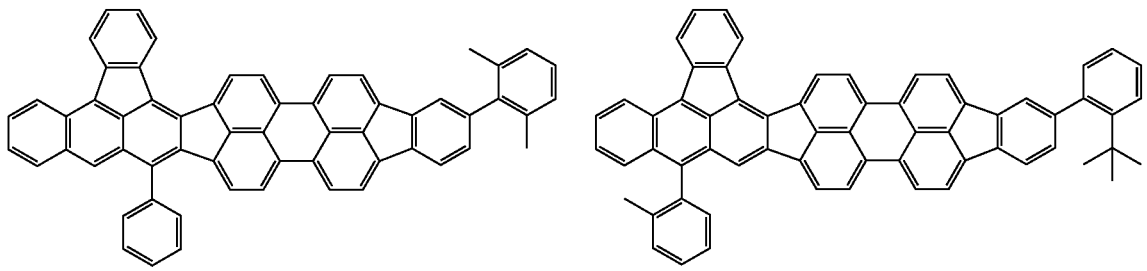
B7 B8
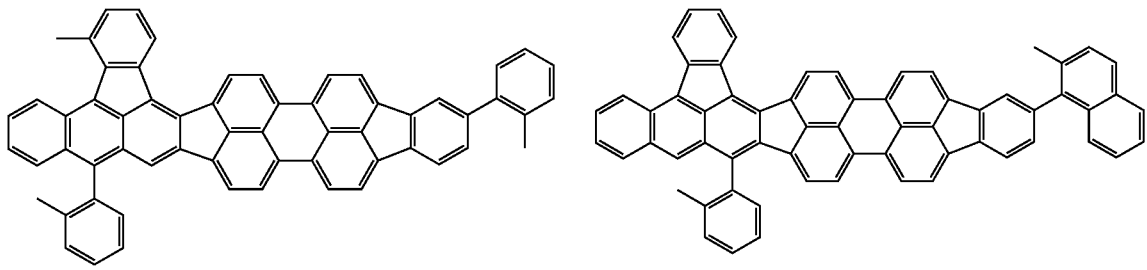

-continued
B9
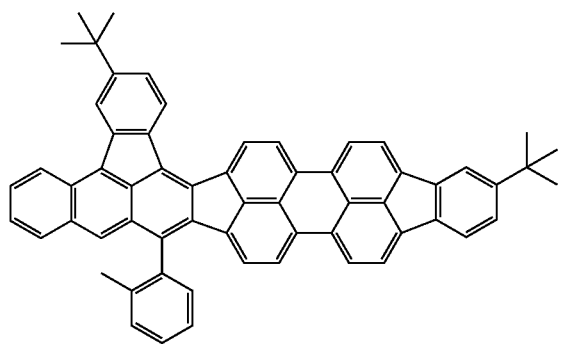
B10
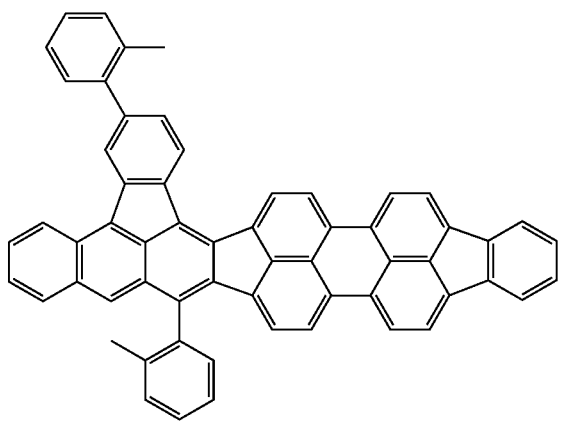
B11
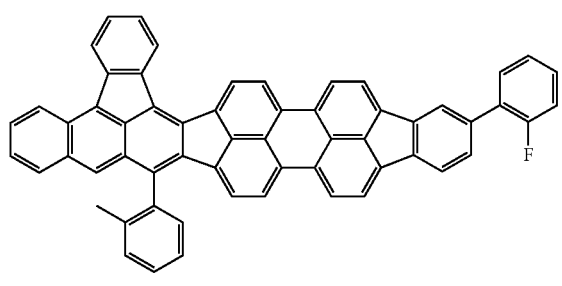
B12
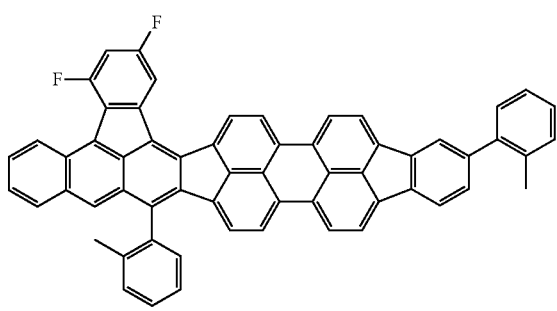
B13
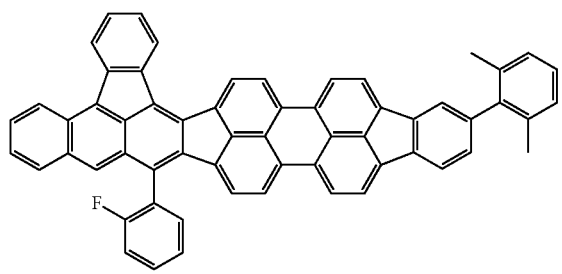
B14
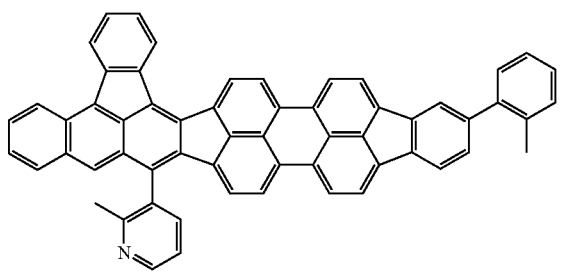
B15
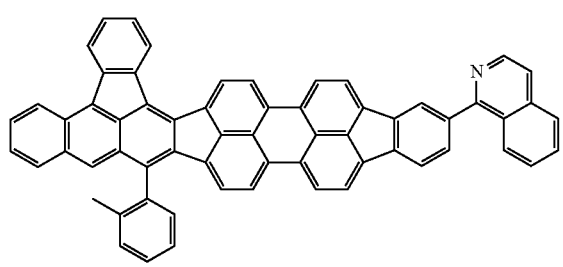

-continued
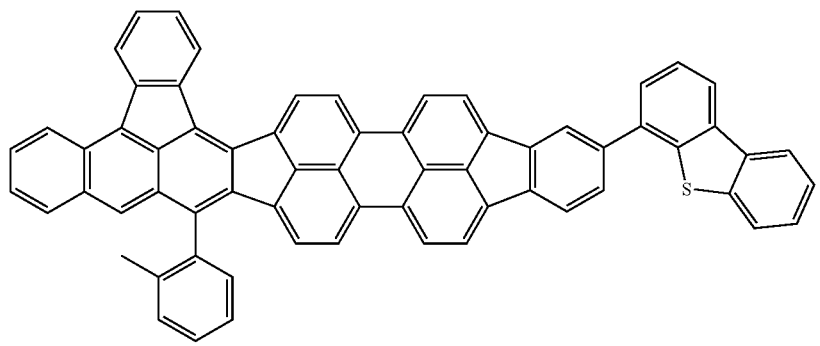
B16
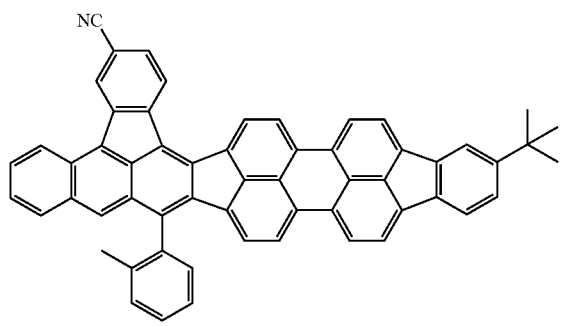
B17
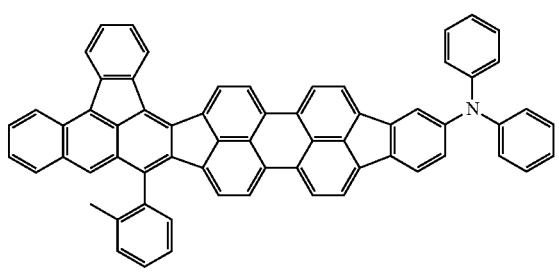
B18
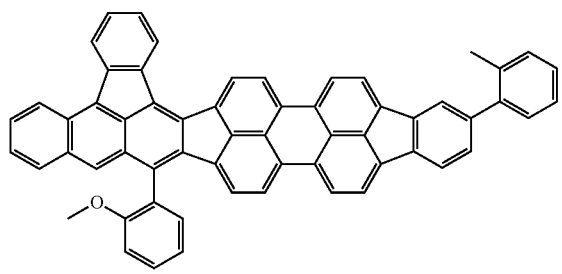
B19
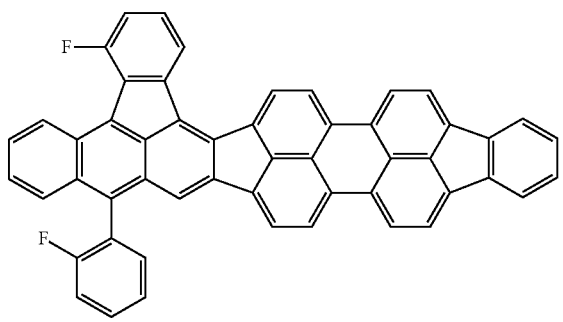
B20
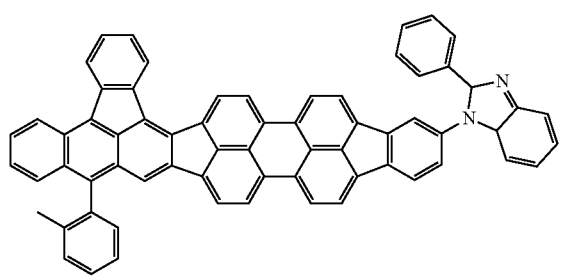
B21
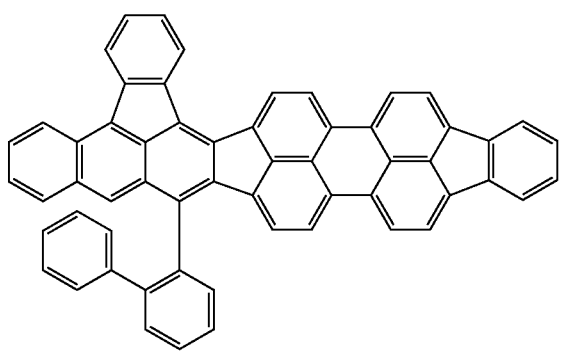
C1

-continued
C2
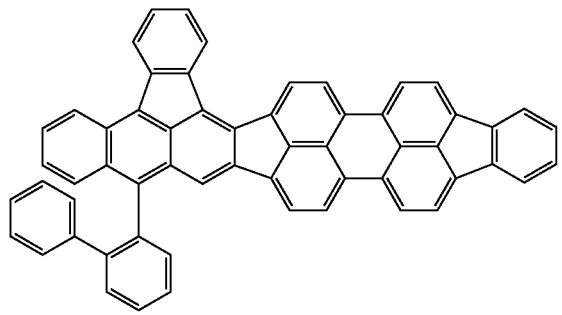
C3
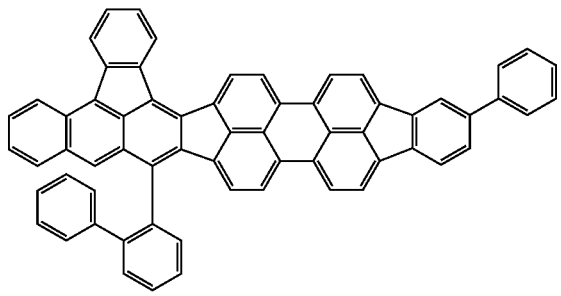
C4
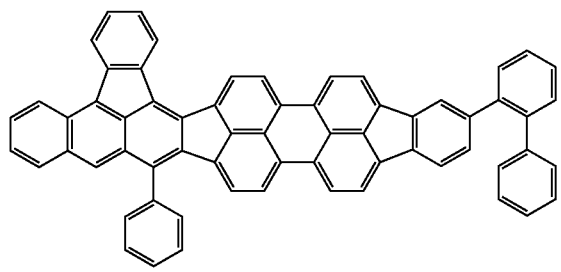
C5
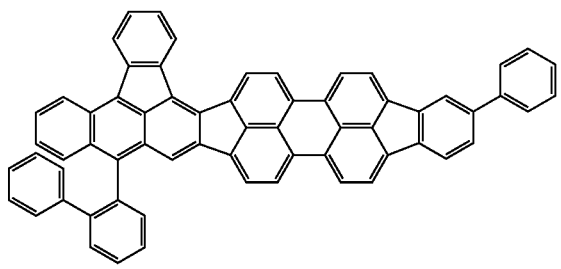
C6
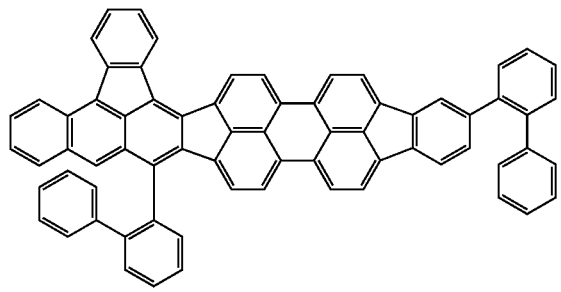
C7
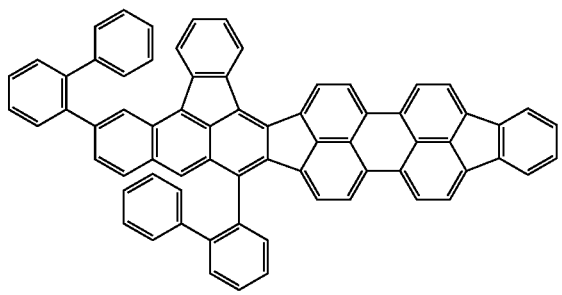
C8
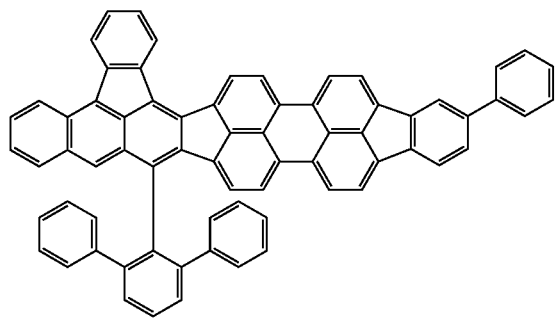
C9
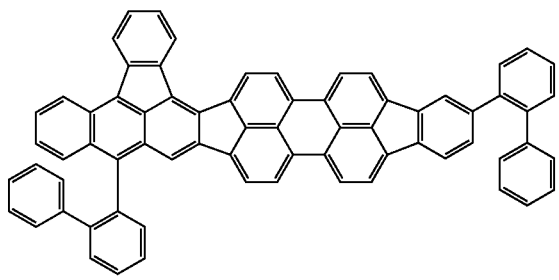

-continued
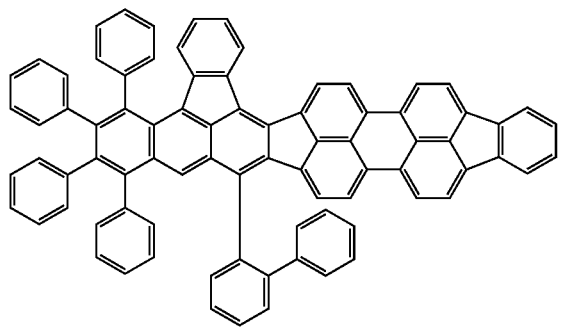
C10
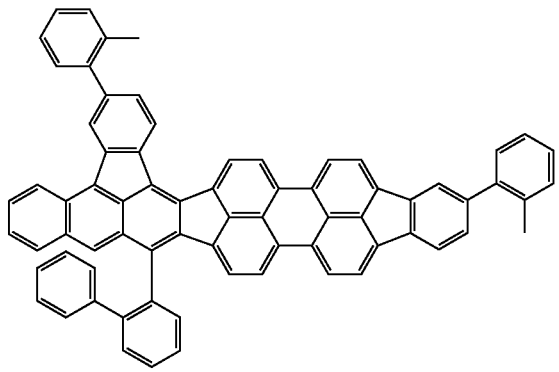
C11
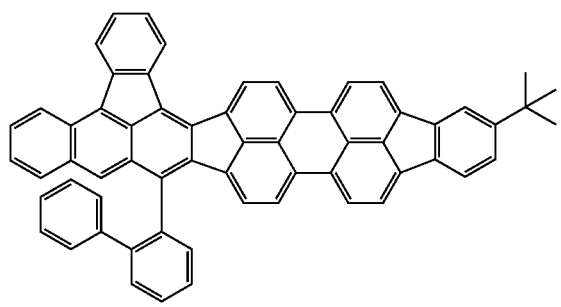
C12
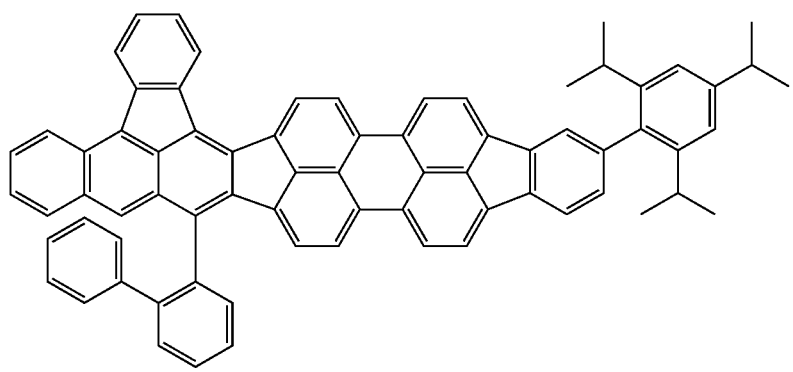
C13
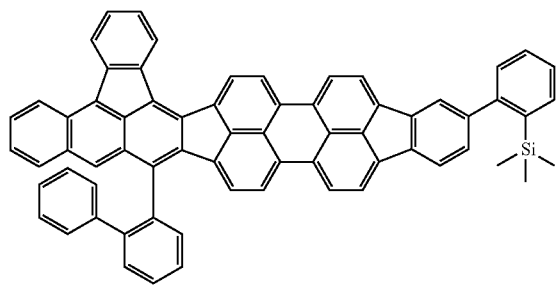
C14
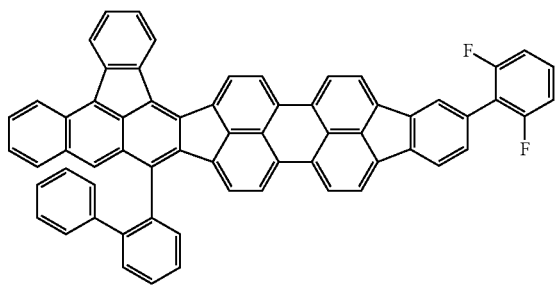
C15

-continued
C16
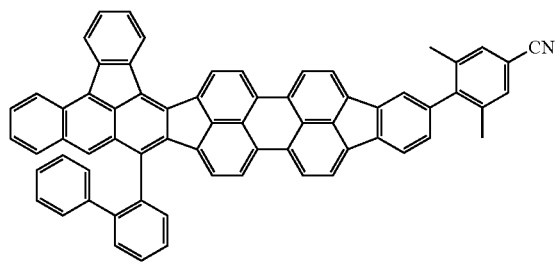
C17
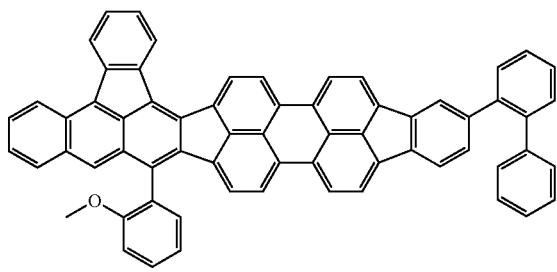
C18
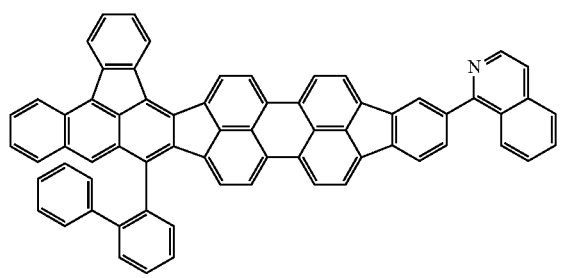
C19
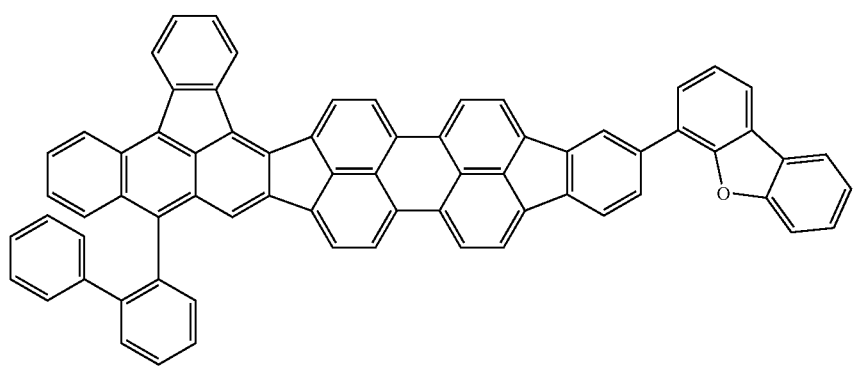
C20
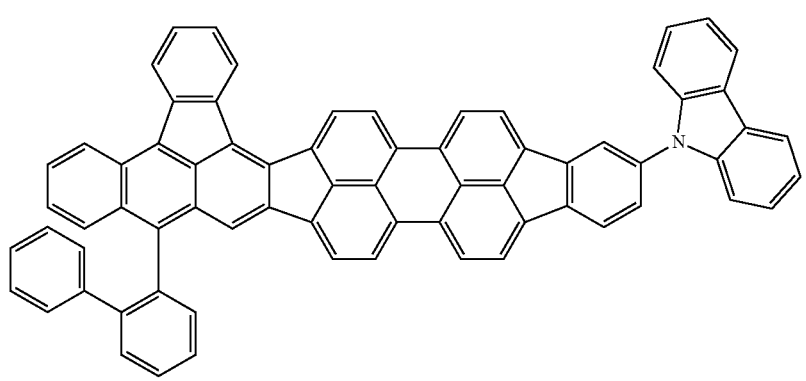

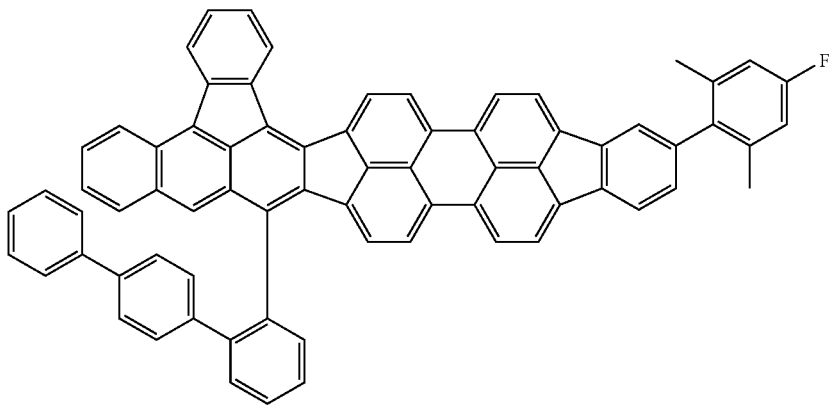

C21

Among the above exemplary compounds, the exemplary compounds A1 to A9 and C1 to C10 are organic compounds which are constituted by only aryl groups. Herein, the compounds which are constituted by only aryl groups have a low HOMO energy level. Therefore, the compounds that belong to the A group are compounds having a high oxidation potential, that is, compounds having high oxidation resistance.

Therefore, among the compounds represented by the formula (1), the organic compounds in which the substituent is constituted by only an aryl group, that is, the exemplary compounds A1 to A9 and C1 to C10 may be used because of their high molecular stability. The compounds that belong to the A group can also be used for light-emitting-layer hosts, carrier transport layers, and carrier injection layers.

Among the above exemplary compounds, the exemplary compounds A10 to A18, B1 to B21, and C1 to C21 are organic compounds in which at least one of an alkyl group, fluorine, an alkoxy group, an amino group, a heterocyclic group having 7 or more carbon atoms, an aryloxy group, a silyl group, and a cyano group is introduced as a substituent. In the organic compound in which an alkyl group or fluorine is introduced, the crystallization is reduced and the sublimation temperature is low. The intermolecular stacking is suppressed, and therefore the concentration quenching can be suppressed when the organic compound is used as a light-emitting-layer guest.

Such an organic compound can be used as a coating material because of its high solubility. The organic compound in which an alkoxy group, an aryloxy group, or a silyl group is introduced also has an effect of suppressing the concentration quenching and thus can be used as a coating material.

The organic compound having a nitrogen-containing heterocyclic group or a cyano group as a substituent among the organic compounds represented by the formula (1) has a low HOMO energy level and higher oxidation resistance. The nitrogen-containing heterocyclic group or the cyano group has an effect of attracting electrons of the basic skeleton.

The organic compound having an amino group as a substituent is a compound that has a narrow band gap and emits light having a longer wavelength. The amino group has an effect of donating electrons.

The organic compound having a heterocyclic group having 7 or more carbon atoms has a higher glass transition temperature than compounds having a phenyl group as a substituent. When such an organic compound is used for light-emitting-layer hosts or carrier transport layers, a thermally stable amorphous film can be formed.

Among the above exemplary compounds, the organic compounds that belong to the B group have a phenyl group introduced to the basic skeleton. Any of an alkyl group, a fluorine atom, an alkoxy group, and a cyano group is introduced at an ortho position of the phenyl group. When a substituent is introduced at an ortho position of the phenyl group, the phenyl group is twisted with respect to the basic skeleton and the substituent at the ortho position covers the it-conjugated plane of the basic skeleton. This reduces the crystallization and suppresses the intermolecular stacking, and thus high sublimability is achieved. When such an organic compound is used as a light-emitting-layer guest, the concentration quenching can be suppressed.

Among the above exemplary compounds, the organic compounds that belong to the C group have a phenyl group introduced to the basic skeleton, and another phenyl group is further introduced at an ortho position of the phenyl group. The organic compounds have a larger effect of covering the i-conjugated plane of the basic skeleton than the organic compounds that belong to the B group. Therefore, the crystallization is further reduced, and the intermolecular stacking is further suppressed and high sublimability is achieved compared with the organic compounds that belong to the B group.

Next, an organic light-emitting element according to an embodiment of the present disclosure will be described.

The organic light-emitting element according to an embodiment of the present disclosure at least includes an anode and a cathode, which are a pair of electrodes, and an organic compound layer disposed between the electrodes. In the organic light-emitting element according to an embodiment of the present disclosure, the organic compound layer may be a single layer or a layered body including a plurality of layers as long as the organic compound layer includes a light-emitting layer.

When the organic compound layer is a layered body including a plurality of layers, the organic compound layer may include, in addition to the light-emitting layer, a hole injection layer, a hole transport layer, an electron blocking layer, a hole/exciton blocking layer, an electron transport layer, and an electron injection layer. The light-emitting layer may be a single layer or a layered body including a plurality of layers.

In the organic light-emitting element according to an embodiment of the present disclosure, at least one layer in the organic compound layer contains the organic compound according to an embodiment of the present disclosure. Specifically, the organic compound represented by the formula (1) is contained in any of the light-emitting layer, the hole injection layer, the hole transport layer, the electron blocking layer, the light-emitting layer, the hole/exciton blocking layer, the electron transport layer, and the electron injection layer. The organic compound represented by the formula (1) is preferably contained in the light-emitting layer. In this case, the emission color of the organic light-emitting element is not particularly limited. The emission color may be any of the three primary colors, white, or an intermediate color.

In the organic light-emitting element according to an embodiment of the present disclosure, when the organic compound represented by the formula (1) is contained in the light-emitting layer, the light-emitting layer may be a layer formed of only the organic compound represented by the formula (1) or a layer formed of the organic compound represented by the formula (1) and other compounds. When the light-emitting layer is a layer formed of the organic compound represented by the formula (1) and other components, the organic compound represented by the formula (1) may be used as a host of the light-emitting layer or a guest of the light-emitting layer. Alternatively, the organic compound may be used as an assist that can be contained in the light-emitting layer.

Herein, the host refers to a compound having the highest weight ratio among the compounds that form the light-emitting layer. The guest refers to a compound that has a lower weight ratio than the host and that is responsible for light emission among the compounds that form the light-emitting layer. The assist refers to a compound that has a lower weight ratio than the host and that assists light emission of the guest among the compounds that form the light-emitting layer. The assist is also referred to as a second host.

When the organic compound represented by the formula (1) is used as a guest of the light-emitting layer, the concentration of the guest is preferably 0.01 wt % or more and 20 wt % or less and more preferably 0.1 wt % or more and 5.0 wt % or less relative to the whole light-emitting layer.

When the organic compound represented by the formula (1) is used as a guest of the light-emitting layer, a material having a higher LUMO energy level than the organic compound (a material having a LUMO energy level closer to the vacuum level) may be used as the host. This is because the organic compound represented by the formula (1) has a low LUMO energy level, and thus when a material having a higher LUMO energy than the organic compound represented by the formula (1) is used as the host, the guest can more readily receive electrons supplied to the host of the light-emitting layer.

As a result of various studies, the present inventors have found that when the organic compound represented by the formula (1) is used as the host or guest of the light-emitting layer, in particular, as the guest of the light-emitting layer, an element that produces an optical output with high efficiently and high luminance and that has very high durability is provided. This light-emitting layer may have a single-layer structure or a multilayer structure. The multilayer structure refers to a state in which the light-emitting layer and another light-emitting layer are stacked. In this case, the emission color of the organic light-emitting element is not limited to red. The emission color may be specifically white or an intermediate color. In the case of white, the other light-emitting layer emits light having a color other than red, such as blue or green. The light-emitting layer is formed by a method such as vapor deposition or coating. The detail of the method will be specifically described in Examples below.

The organic compound represented by the formula (1) may be used in combination with, for example, a publicly known low-molecular-weight or high-molecular-weight hole injection compound or hole transport compound, a compound serving as the host, a luminous compound, an electron injection compound, and an electron transport compound if necessary.

Examples of these compounds will be described below.

A hole injection or transport material may be a material having a high hole mobility so that injection of holes from the anode is facilitated and the injected holes can be transported to the light-emitting layer. The hole injection or transport material may also be a material having a high glass transition temperature in order to suppress the deterioration of the film quality such as crystallization in the organic light-emitting element. Examples of the low-molecular-weight or high-molecular-weight material having hole injectability or transportability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used for the electron blocking layer.

Non-limiting specific examples of the compound used as the hole injection or transport material are shown below.

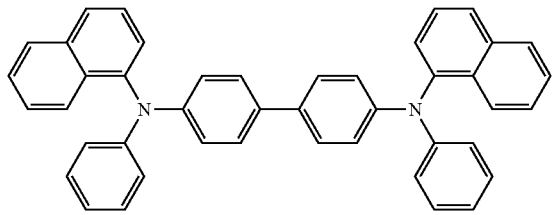

HT1

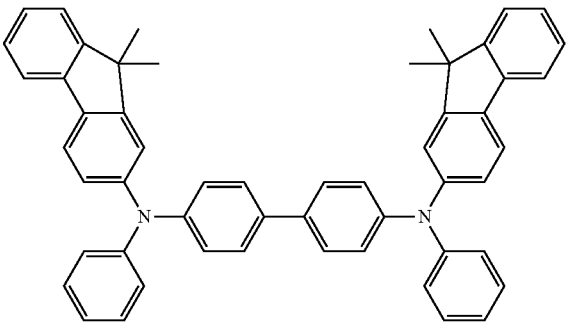

HT2

-continued
HT3
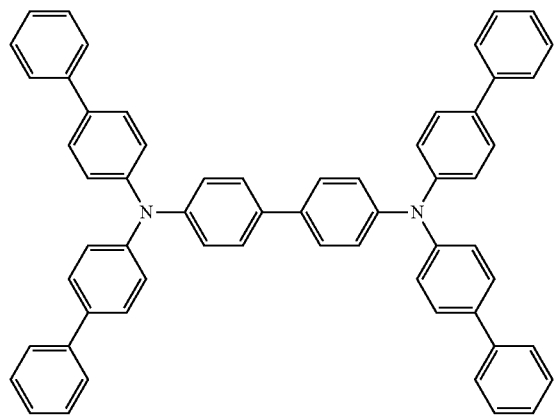
HT4
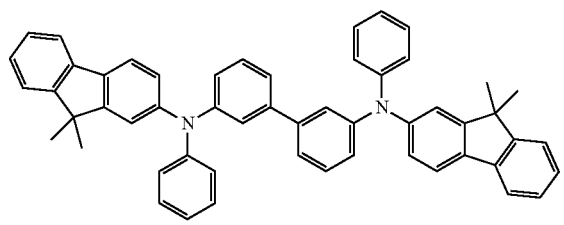
HT5
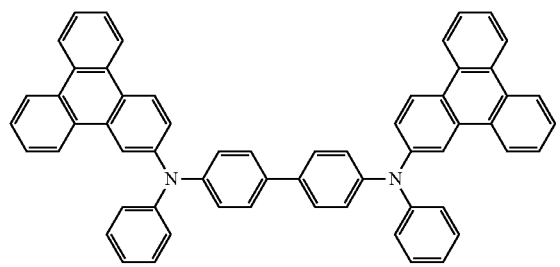
HT6
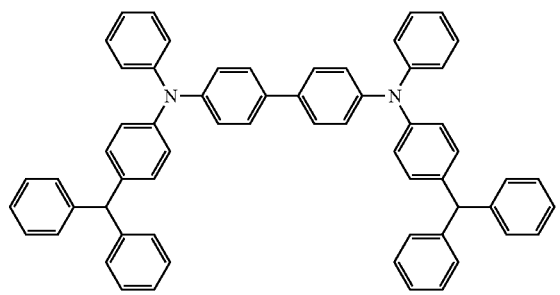
HT7
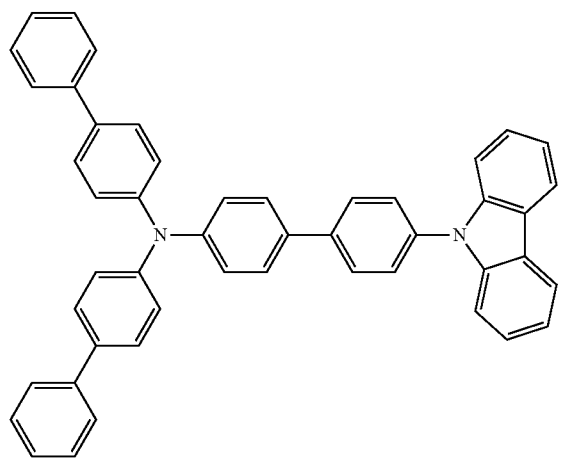
HT8
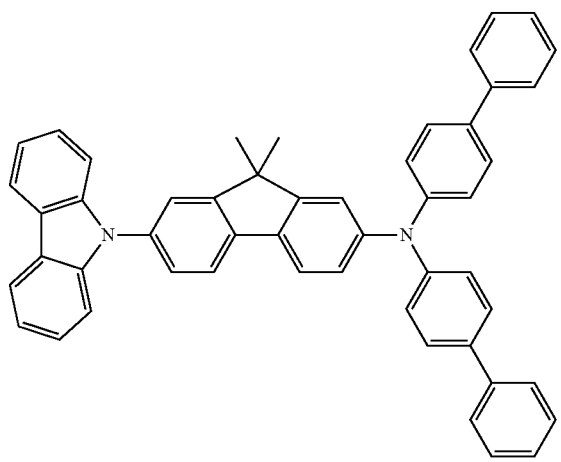

-continued
HT9
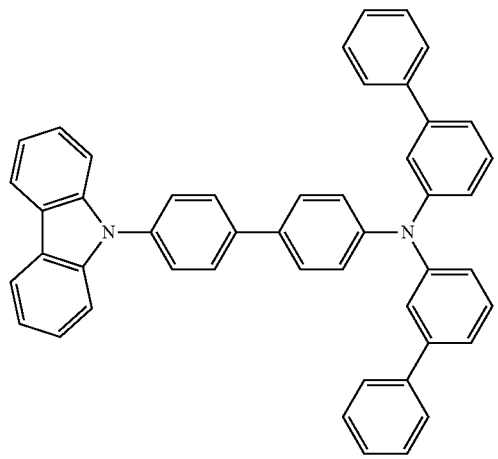
HT10
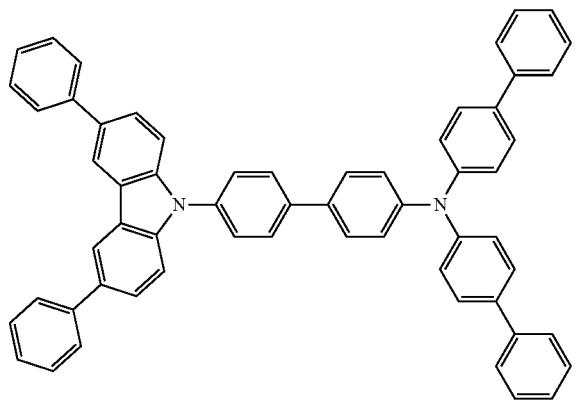
HT11
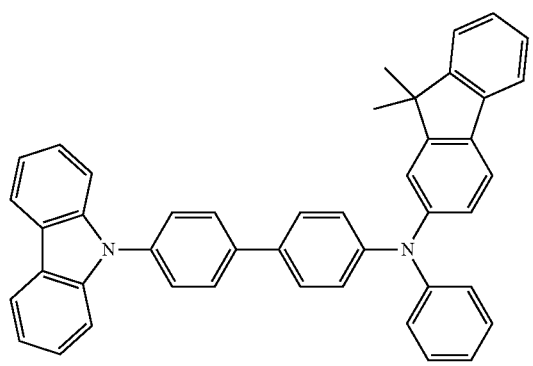
HT12
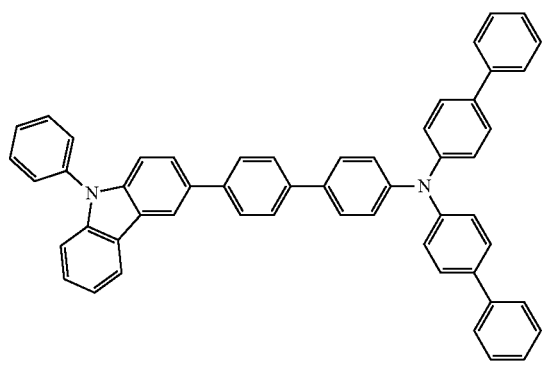
HT13
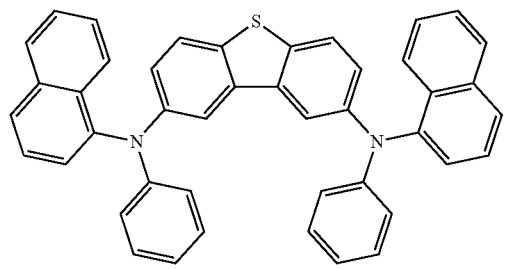
HT14
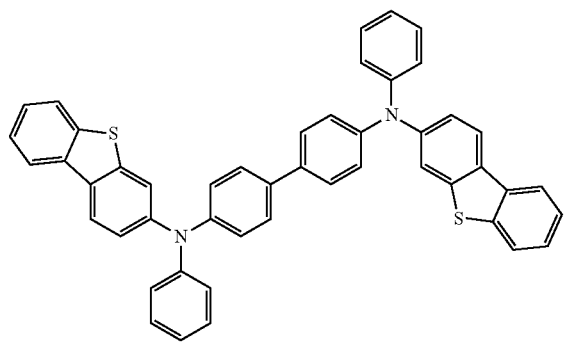
HT15
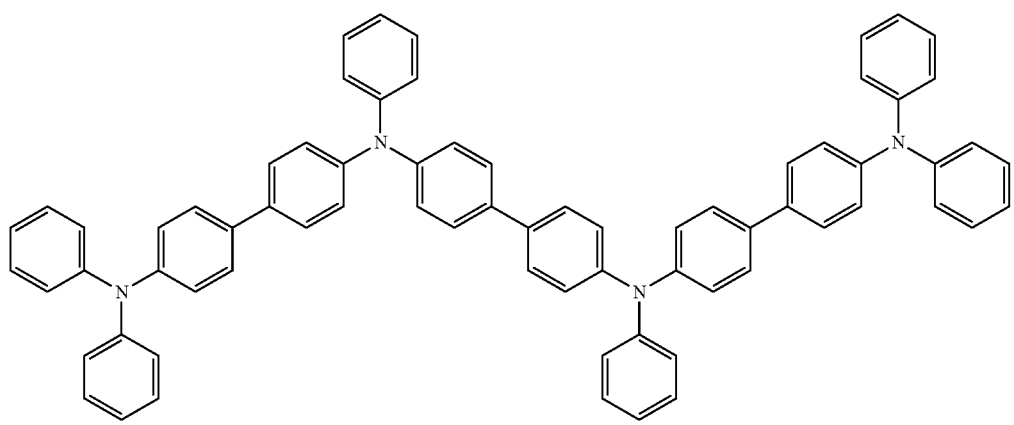

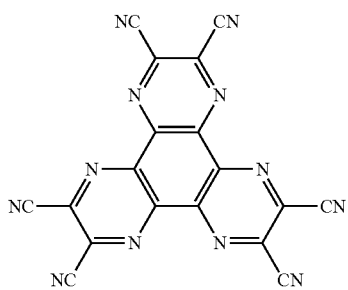
HT16

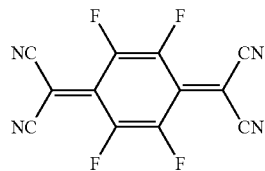
HT17

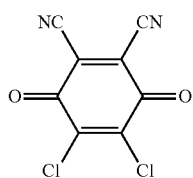
HT18

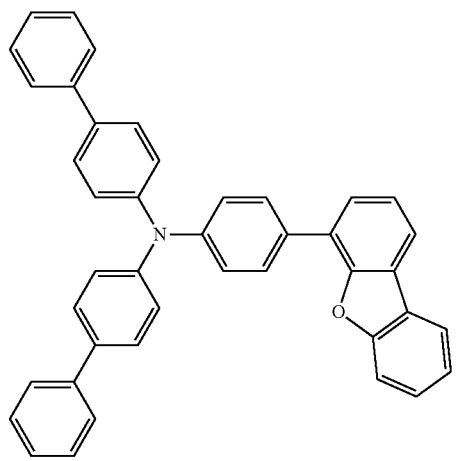
HT19

Examples of the light-emitting material mainly concerned with a light-emitting function include, in addition to the organic compound represented by the formula (1), fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

The organic compound represented by the formula (1) is a compound having a narrow band gap and a low HOMO/LUMO energy level. Therefore, when a mixture layer is formed with another light-emitting material or when light-emitting layers are stacked, the other light-emitting material may also have a low HOMO/LUMO energy level. This is because if the HOMO/LUMO energy level is high, formation of a quenching component or a trap level may occur, such as the case where the other light-emitting material may form an exciplex together with the organic compound represented by the formula (1).

Non-limiting specific examples of the compound used as the light-emitting material are shown below.

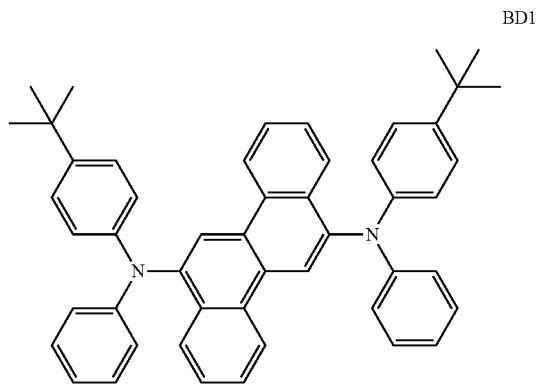
BD1

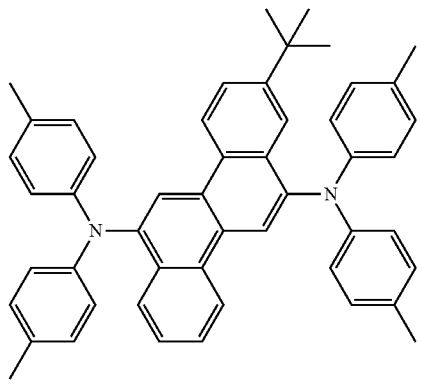
BD2

BD3 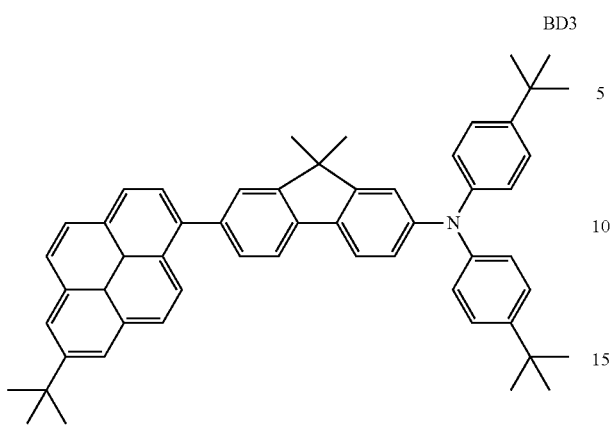
BD4 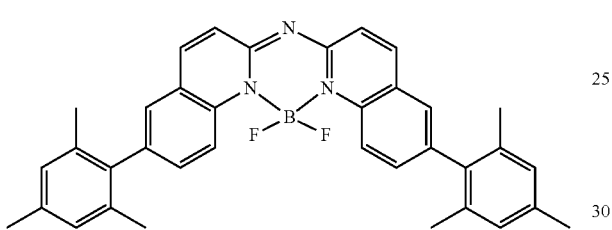
BD5 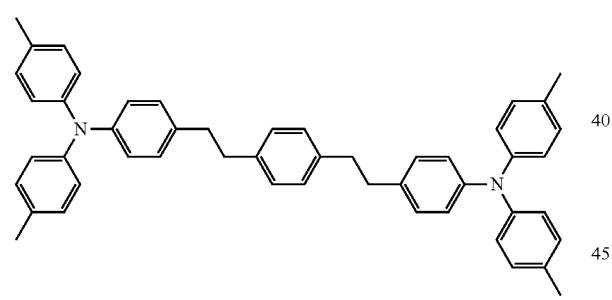
BD6 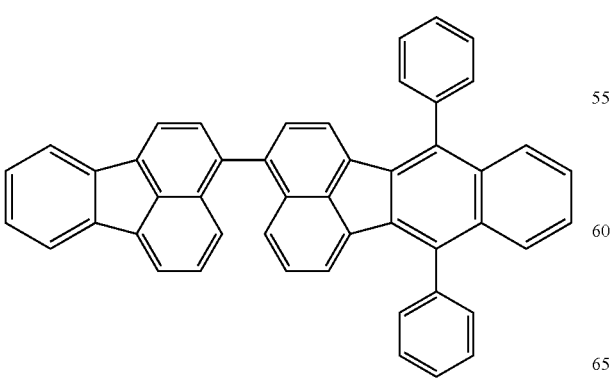
BD7 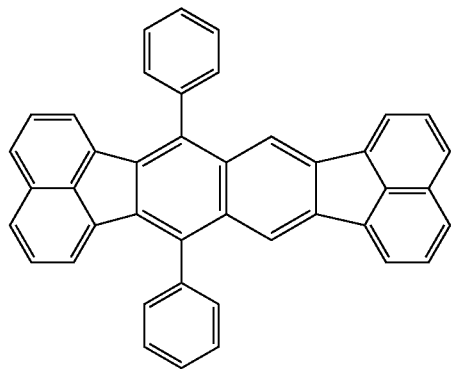
BD8 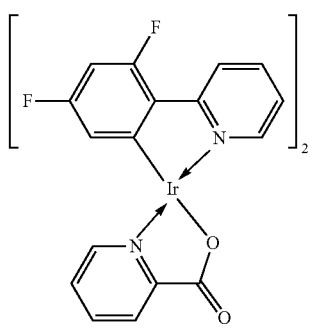
GD1 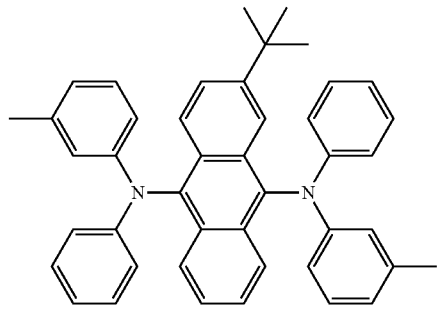
GD2 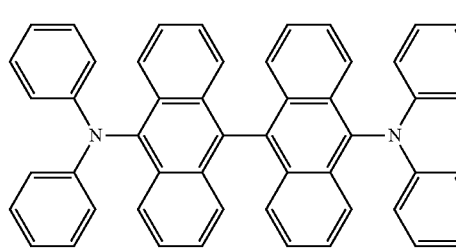
GD3 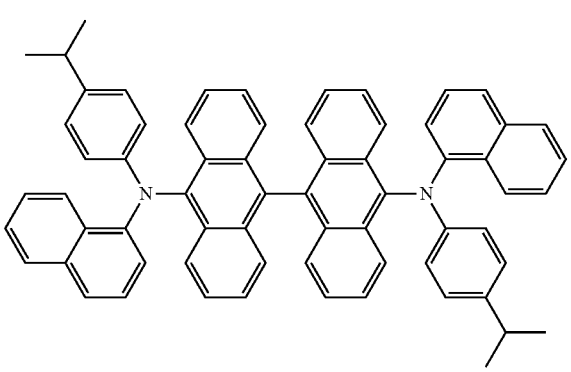

GD4
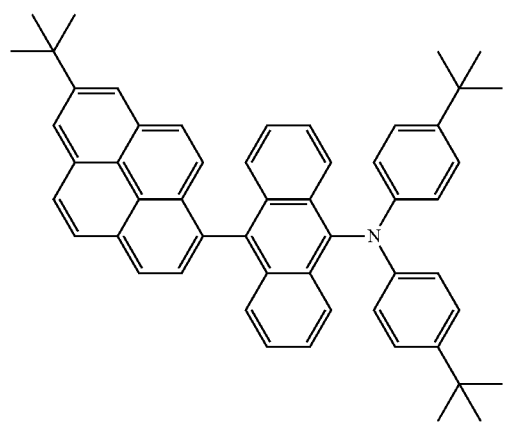
GD5
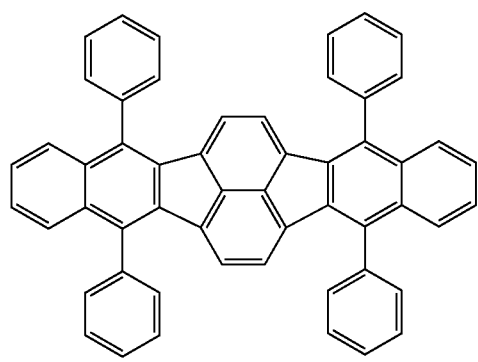
GD6
GD7
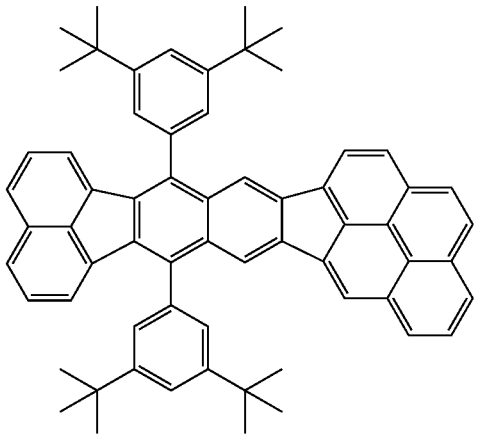
GD8
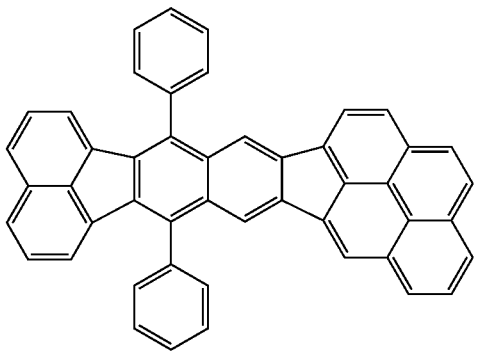
GD9
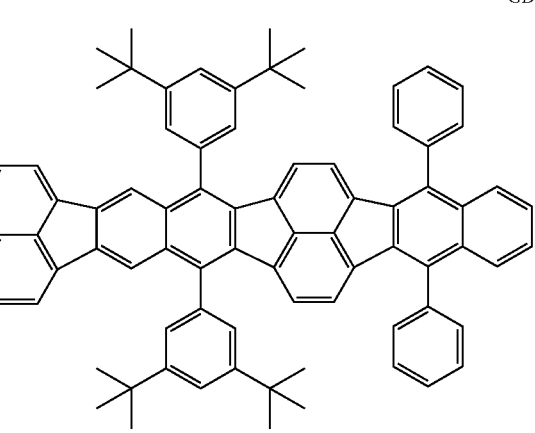
GD10
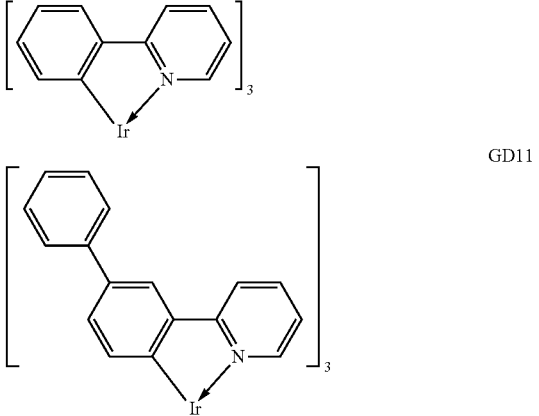
GD11

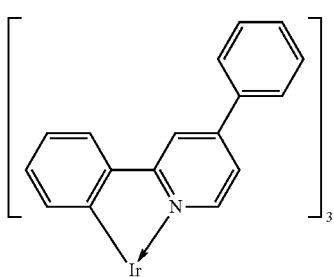

GD12

Examples of the light-emitting-layer host or light emission assist contained in the light-emitting layer include aromatic hydrocarbon compounds and derivatives thereof, carbazole derivatives, dibenzofuran derivatives, dibenzothiophene derivatives, organoaluminum complexes such as tris(8-quinolinolato)aluminum, and organoberyllium complexes.

The organic compound represented by the formula (1) is a compound having a narrow band gap and a low HOMO/LUMO energy level. Therefore, the host material may also be formed of a hydrocarbon and may have a low HOMO/LUMO energy level. This is because if the host material contains a hetero atom such as a nitrogen atom, the HOMO/LUMO energy level increases, and formation of a quenching component or a trap level may occur, such as the case where the host material may form an exciplex together with the organic compound represented by the formula (1).

In particular, the host may have an anthracene, tetracene, perylene, or pyrene skeleton in its molecular skeleton. This is because the host is formed of a hydrocarbon as described above and also has an S1 energy capable of causing sufficient energy transfer to the organic compound according to an embodiment of the present disclosure.

Non-limiting specific examples of the compound used as the light-emitting-layer host or light emission assist material contained in the light-emitting layer are shown below.

EM1

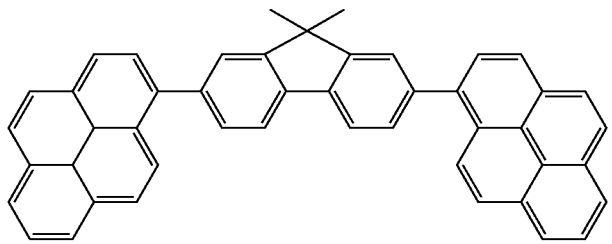

EM2

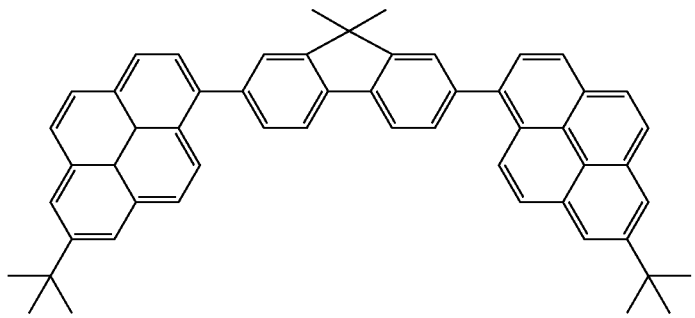

EM3

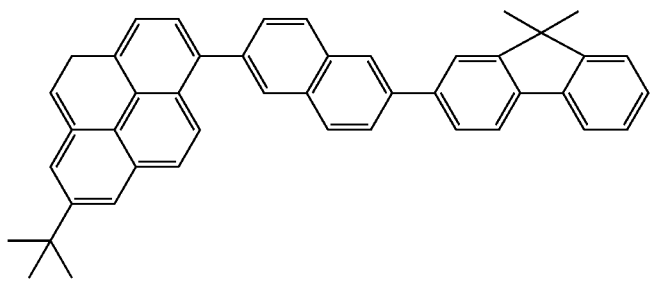

EM4

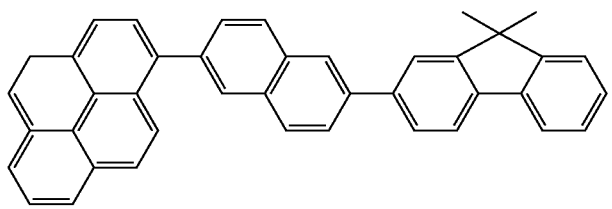

-continued
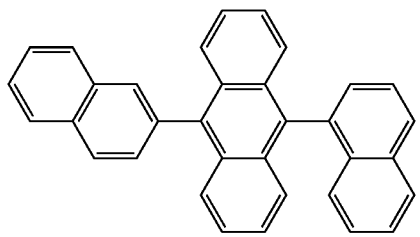
EM5
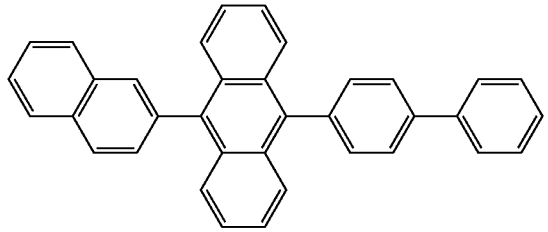
EM6
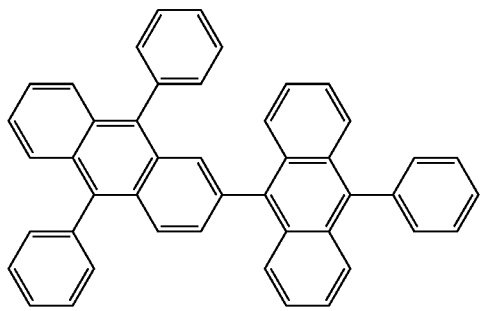
EM7
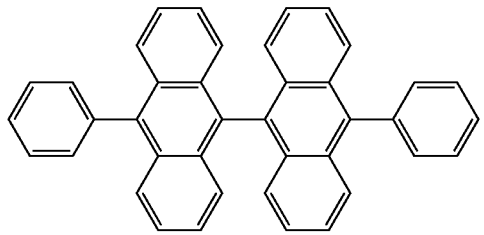
EM8
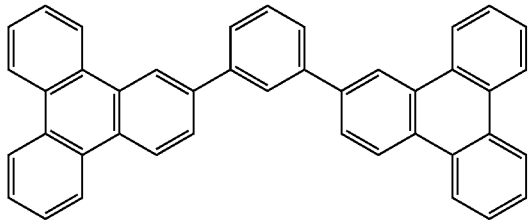
EM9
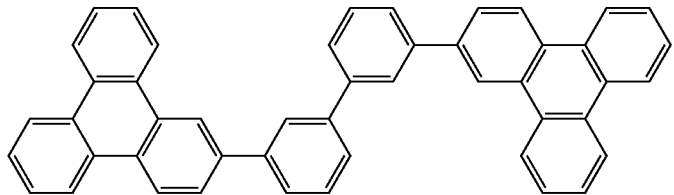
EM10

-continued
EM11
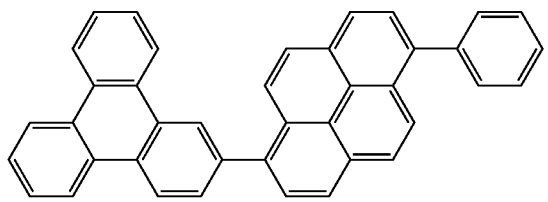
EM12
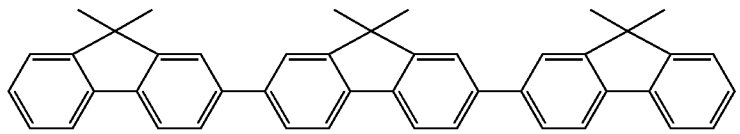
EM13
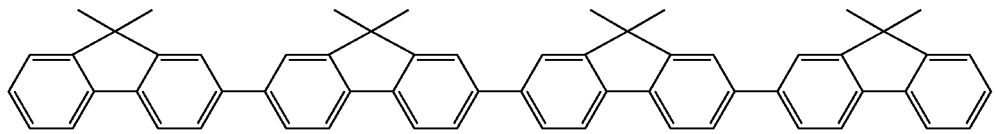
EM14
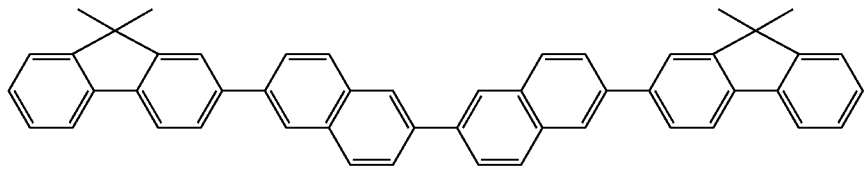
EM15
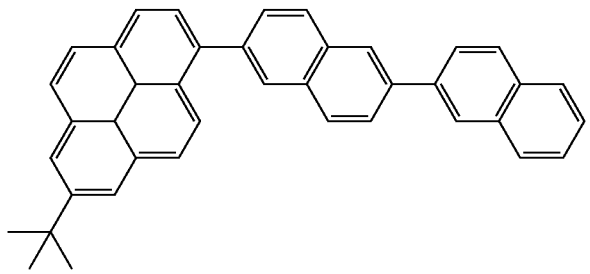
EM16
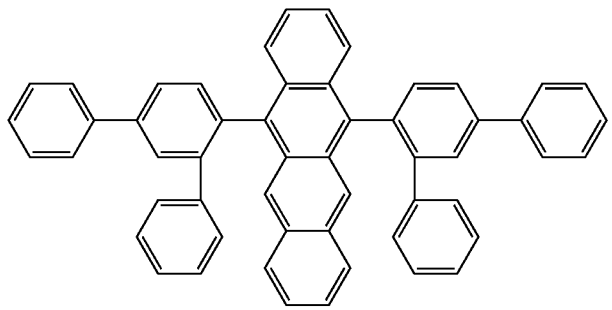
EM17
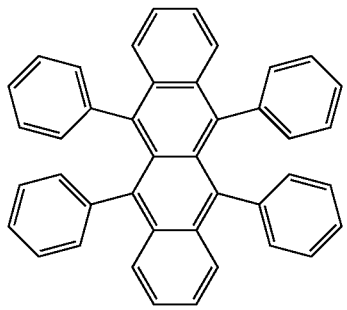

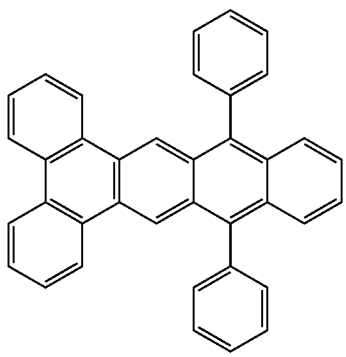
EM18
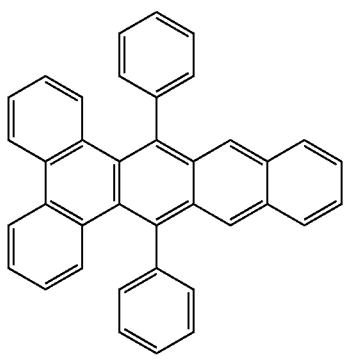
EM19
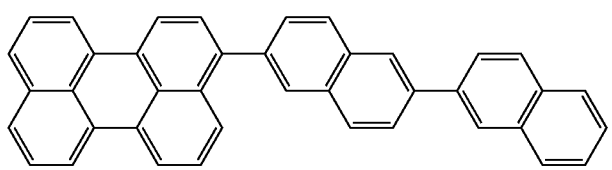
EM20
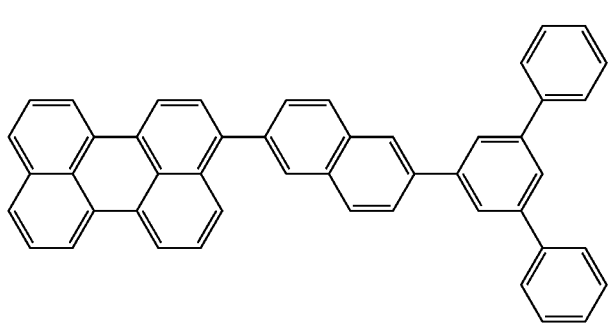
EM21
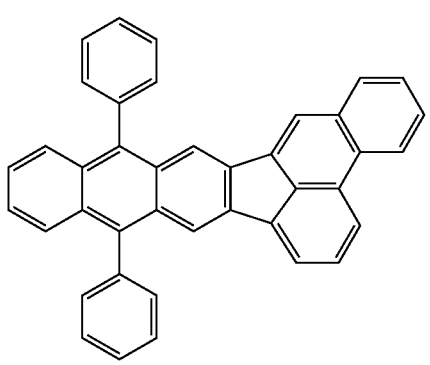
RM22

RM23
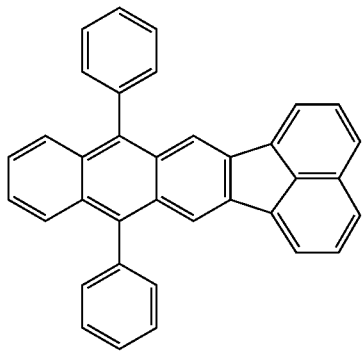
EM24
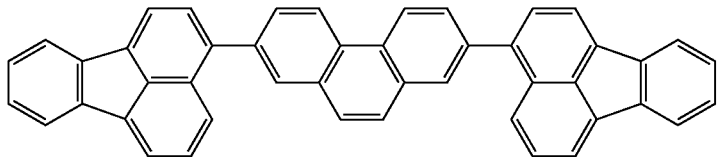
EM25
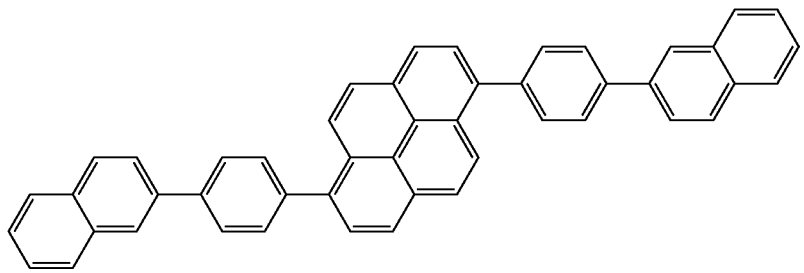
EM26
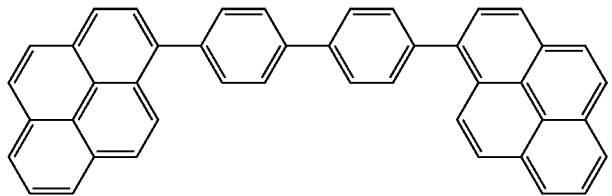
EM27
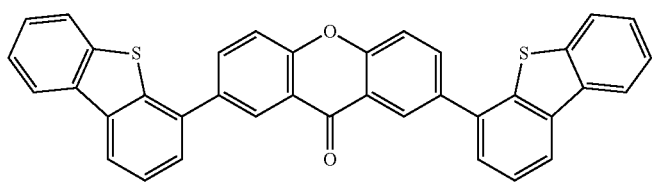
EM28
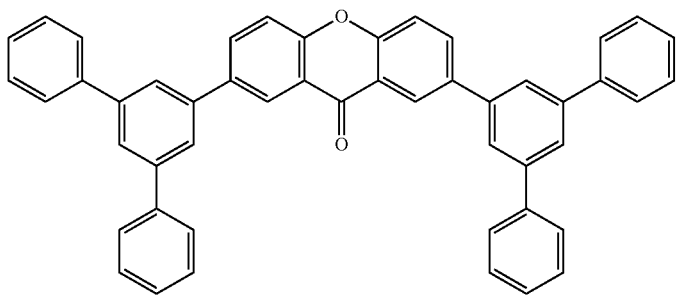

-continued

EM29

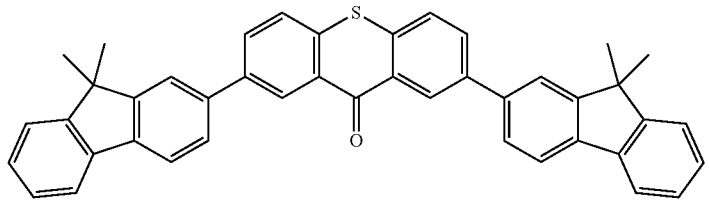

EM30

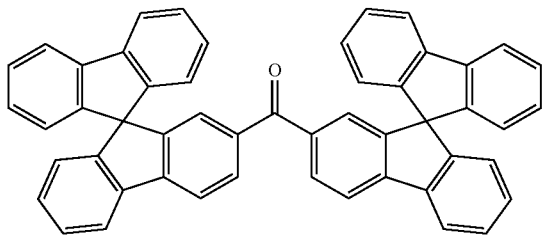

EM31

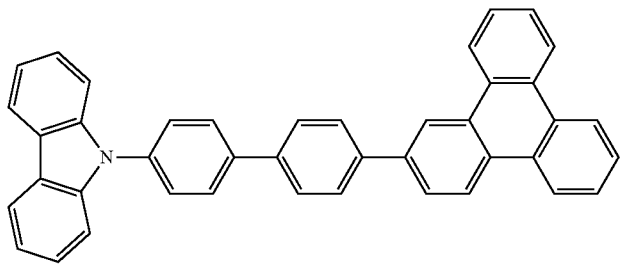

EM32

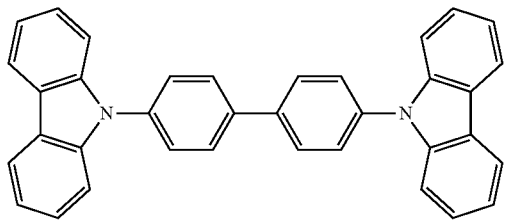

The electron transport material can be freely selected from materials capable of transporting electrons injected from the cathode to the light-emitting layer. The electron transport material is selected in consideration of, for example, the balance with the hole mobility of the hole transport material. Examples of the material having electron transportability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (e.g., fluorene derivatives, naphthalene derivatives, chrysene derivatives, and anthracene derivatives). The above electron transport material is also suitably used for the hole blocking layer.

Non-limiting specific examples of the compound used as the electron transport material are shown below.

ET1

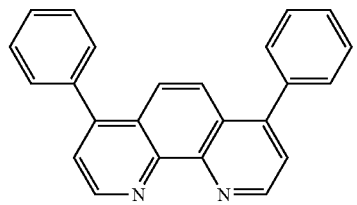

ET2
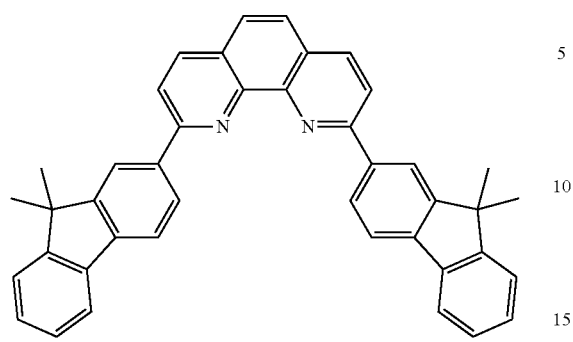
ET3
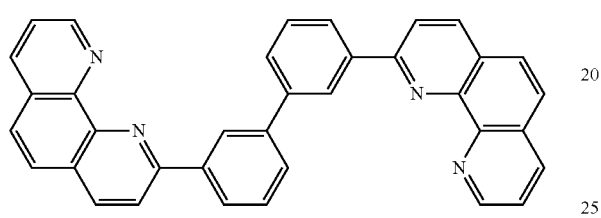
ET4
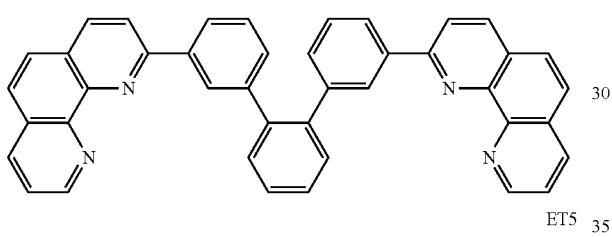
ET5
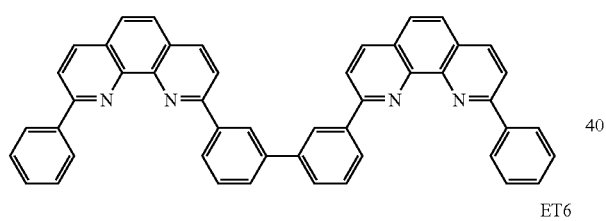
ET6
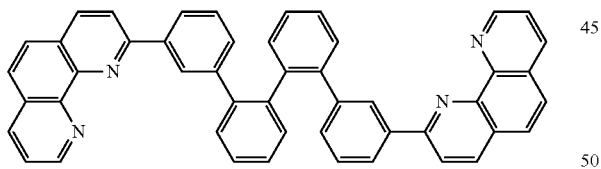
ET7
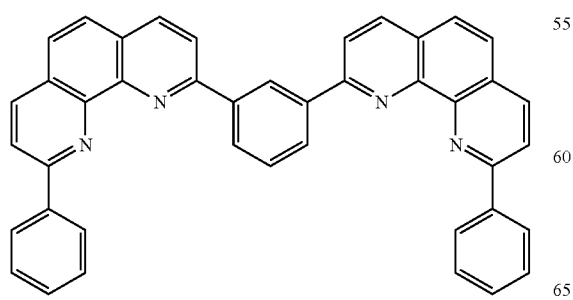
ET8
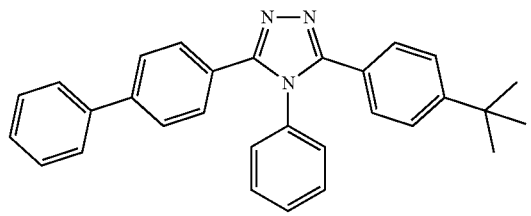
ET9
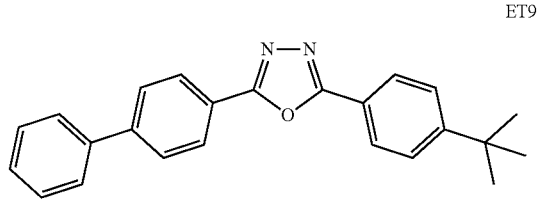
ET10
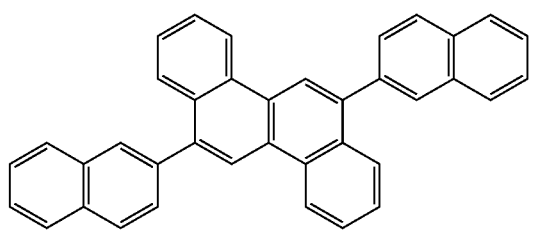
ET11
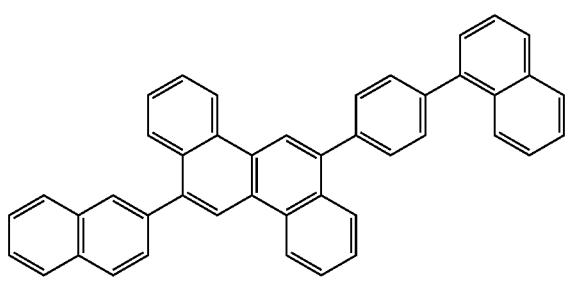
ET12
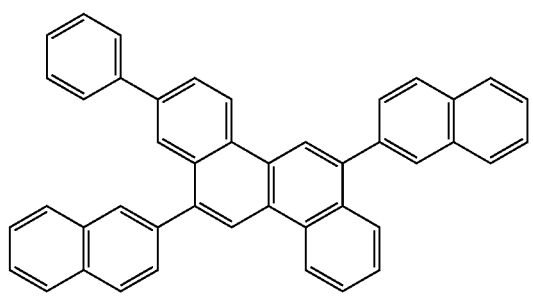

ET13
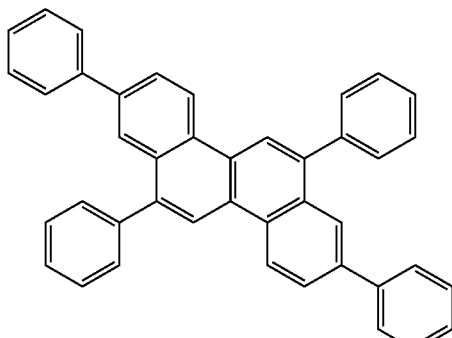
ET14
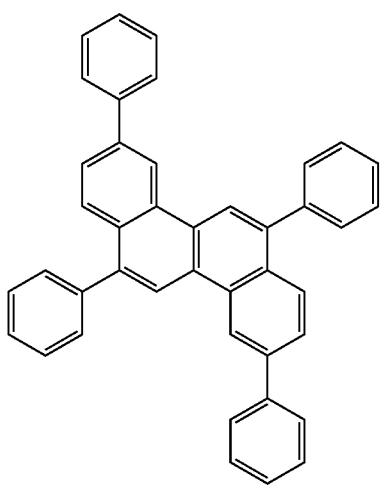
ET15
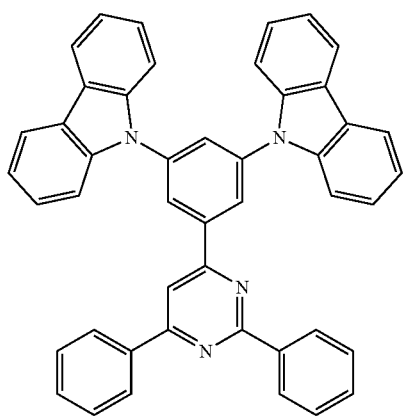
ET16
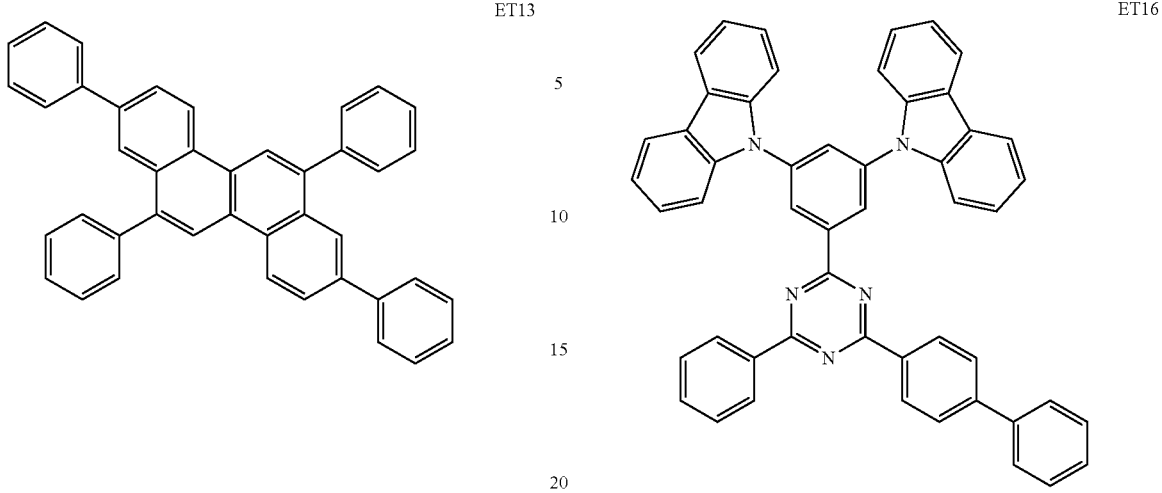
ET17
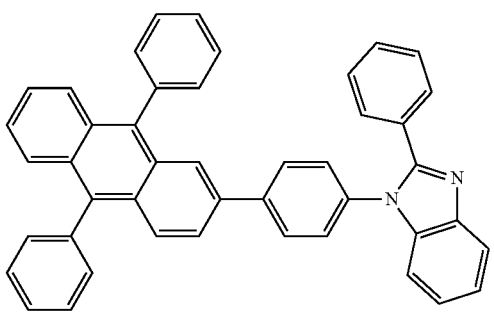
ET18
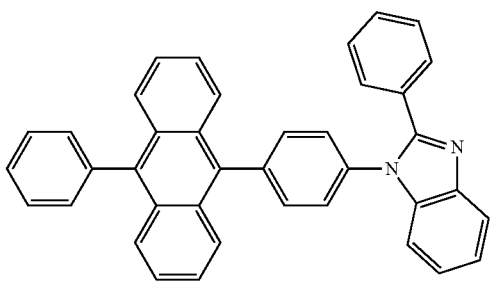
ET19
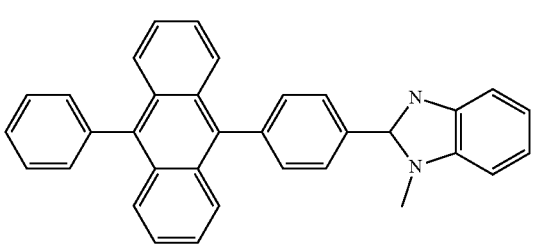

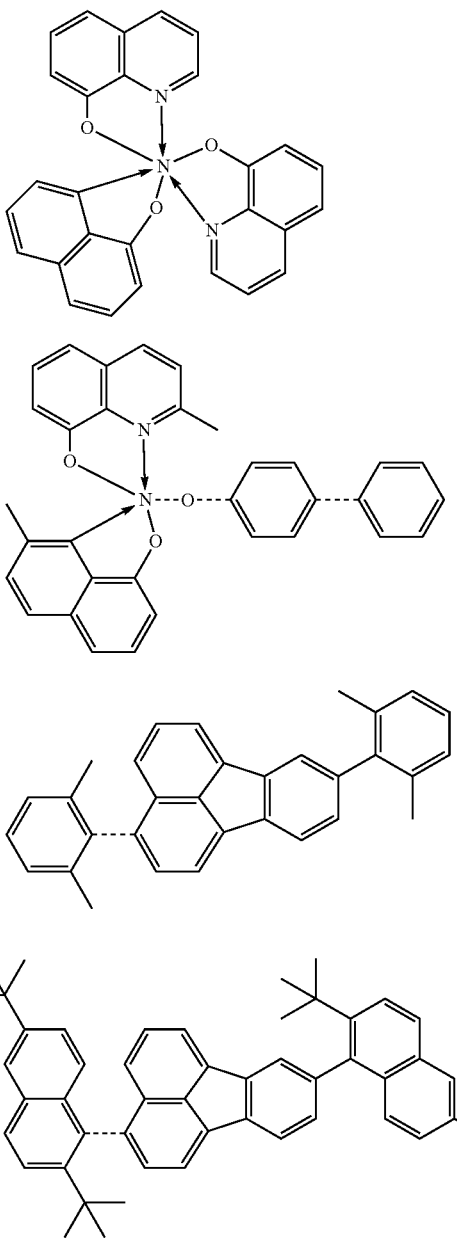

Configuration of Organic Light-Emitting Element

An organic light-emitting element is obtained by forming an anode, an organic compound layer, and a cathode on a substrate. For example, a protective layer and a color filter may be disposed on the cathode. If the color filter is disposed, a planarizing layer may be disposed.

Examples of the material for the substrate include quartz, glass, silicon wafers, resins, and metals. A switching element such as a transistor and a wiring line may be disposed on the substrate, and an insulating layer may be disposed thereon. The insulating layer may be formed of any material as long as contact holes can be formed to establish electrical connection between the anode and the wiring line and the anode can be insulated from wiring lines to which the anode is not connected. Examples of the material for the insulating layer include resins such as polyimide, silicon oxide, and silicon nitride.

The material for the anode desirably has as high a work function as possible. Examples of the material for the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Conductive polymers such as polyaniline, polypyrrole, and polythiophene can also be used.

These electrode materials may be used alone or in combination of two or more. The anode may have a single-layer structure or a multilayer structure.

When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the transparent electrode is not limited thereto. The electrode can be formed by photolithography.

On the other hand, the material for the cathode desirably has a low work function. Examples of the material for the cathode include alkali metals such as lithium; alkaline earth metals such as calcium; elemental metals such as aluminum, titanium, manganese, silver, lead, and chromium; mixtures containing these metals; alloys of these metals, such as magnesium-silver, aluminum-lithium, aluminum-magnesium, silver-copper, and zinc-silver; and metal oxides such as indium tin oxide (ITO). These electrode materials may be used alone or in combination of two or more. The cathode may have a single-layer structure or a multilayer structure. In particular, silver is preferably used and a silver alloy is more preferably used to suppress aggregation of silver. The silver alloy may have any mixing ratio such as 1:1 as long as the aggregation of silver can be suppressed.

Any device may be employed, such as a top emission device obtained by using a conductive oxide layer made of, for example, ITO as a cathode or a bottom emission device obtained by using a reflective electrode made of, for example, aluminum (Al) as a cathode. The cathode may be formed by any method such as a DC and AC sputtering method. In this method, good film coverage can be achieved to readily reduce the resistance.

After the formation of the cathode, a protective layer may be disposed. For example, a glass plate including a moisture absorbent is bonded to the cathode. This suppresses permeation of water or the like into the organic compound layer and thus can suppress occurrence of display defects. In another embodiment, a passivation film made of silicon nitride or the like may be disposed on the cathode to suppress permeation of water or the like into an organic EL layer. For example, after the formation of the cathode, the resulting substrate may be transferred to another chamber without breaking the vacuum, and a silicon nitride film having a thickness of 2 μm may be formed by a chemical vapor deposition (CVD) method to provide a protective layer. After the film formation by the CVD method, a protective layer may be disposed by an atomic layer deposition method (ALD method).

A color filter may be disposed on each pixel. For example, color filters each having a size corresponding to the pixel size may be disposed on another substrate, and this substrate may be bonded to the substrate on which the organic light-emitting elements have been disposed. Alternatively, a color filter may be patterned on a protective layer made of silicon oxide or the like using photolithography.

The organic compound layers (e.g., a hole injection layer, a hole transport layer, an electron blocking layer, a light-emitting layer, a hole blocking layer, an electron transport layer, and an electron injection layer) that constitute the organic light-emitting element according to an embodiment of the present disclosure are formed by the following method.

The organic compound layers that constitute the organic light-emitting element according to an embodiment of the present disclosure can be formed by a dry process such as a vacuum vapor deposition method, an ionized vapor deposition method, a sputtering method, or a method using plasma. Instead of the dry process, a wet process in which an organic compound is dissolved in an appropriate solvent and a layer is formed by a publicly known coating method (e.g., spin coating, dipping, a casting method, a Langmuir-Blodgett (LB) method, or an ink jet method) can also be employed.

When a layer is formed by, for example, a vacuum vapor deposition method or a solution coating method, crystallization or the like is unlikely to occur and the resulting layer has high stability over time. When a layer is formed by a coating method, the layer can be formed by using an appropriate binder resin in combination.

Non-limiting examples of the binder resin include polyvinylcarbazole resin, polycarbonate resin, polyester resin, ABS resin, acrylic resin, polyimide resin, phenolic resin, epoxy resin, silicone resin, and urea resin.

These binder resins may be used alone as a homopolymer or a copolymer or in combination as a mixture of two or more. Furthermore, publicly known additives such as a plasticizer, an antioxidant, and an ultraviolet absorber may be optionally used in combination.

Applications of Organic Light-Emitting Element According to Embodiment of the Present Disclosure The organic light-emitting element according to an embodiment of the present disclosure can be used as a member of display apparatuses and lighting apparatuses. In addition, the organic light-emitting element may be used as, for example, an exposure light source for electrophotographic image forming apparatuses, a backlight of liquid crystal display apparatuses, and a light-emitting device including a white light source having a color filter.

The display apparatus may be an image information processing apparatus that includes an image input unit which inputs image information from an area CCD, a linear CCD, a memory card, or the like and an information processing unit which processes the input information and that displays the input image on a display unit.

The display unit included in an image pickup apparatus or an ink jet printer may have a touch panel function. The touch panel function may be driven by any method such as a method that uses infrared rays, electrostatic capacitance, a resistive film, or electromagnetic induction. The display apparatus may be used as a display unit of multifunction printers.

Next, a display apparatus according to an embodiment of the present disclosure will be described with reference to the attached drawings. FIG. 3 is a schematic sectional view illustrating an example of a display apparatus including organic light-emitting elements and TFT elements connected to the organic light-emitting elements. The TFT elements are an example of active elements.

A display apparatus 10 in FIG. 3 includes a substrate 11 made of glass or the like and a moistureproof film 12 that is disposed on the substrate 11 and protects a TFT element or an organic compound layer. A metal gate electrode 13, a gate insulating film 14, and a semiconductor layer 15 are disposed.

A TFT element 18 includes a semiconductor layer 15, a drain electrode 16, and a source electrode 17. An insulating film 19 is disposed on the TFT element 18. An anode 21 that constitutes an organic light-emitting element and the source electrode 17 are connected to each other through a contact hole 20.

The form of electrical connection between electrodes (anode and cathode) included in the organic light-emitting element and electrodes (source electrode and drain electrode) included in the TFT is not limited to the form illustrated in FIG. 3. That is, one of the anode and the cathode may be electrically connected to one of the source electrode and the drain electrode of the TFT element.

In the display apparatus 10 in FIG. 3, an organic compound layer 22 is illustrated as if having a single-layer structure, but may have a multilayer structure. A first protective layer 24 and a second protective layer 25 for suppressing the deterioration of the organic light-emitting element 26 are disposed on a cathode 23.

In the display apparatus 10 in FIG. 3, a transistor is used as a switching element. Instead, an MIM element may be used as a switching element.

The transistor used in the display apparatus 10 in FIG. 3 is not limited to transistors that use a single-crystal silicon wafer, but may be thin-film transistors including an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. The thin-film transistors are also referred to as TFT elements.

The transistor included in the display apparatus 10 in FIG. 3 may be formed in a substrate such as a Si substrate. Herein, the phrase "formed in a substrate" means that a transistor is produced by processing the substrate itself, such as a Si substrate. That is, a transistor formed in a substrate can be regarded as a transistor integrally formed with a substrate.

The resolution is used to decide whether the transistor is formed in a substrate. For example, in the case of a size of 1 inch and a resolution of about QVGA, the transistor may be formed in a Si substrate.

Figure 4:
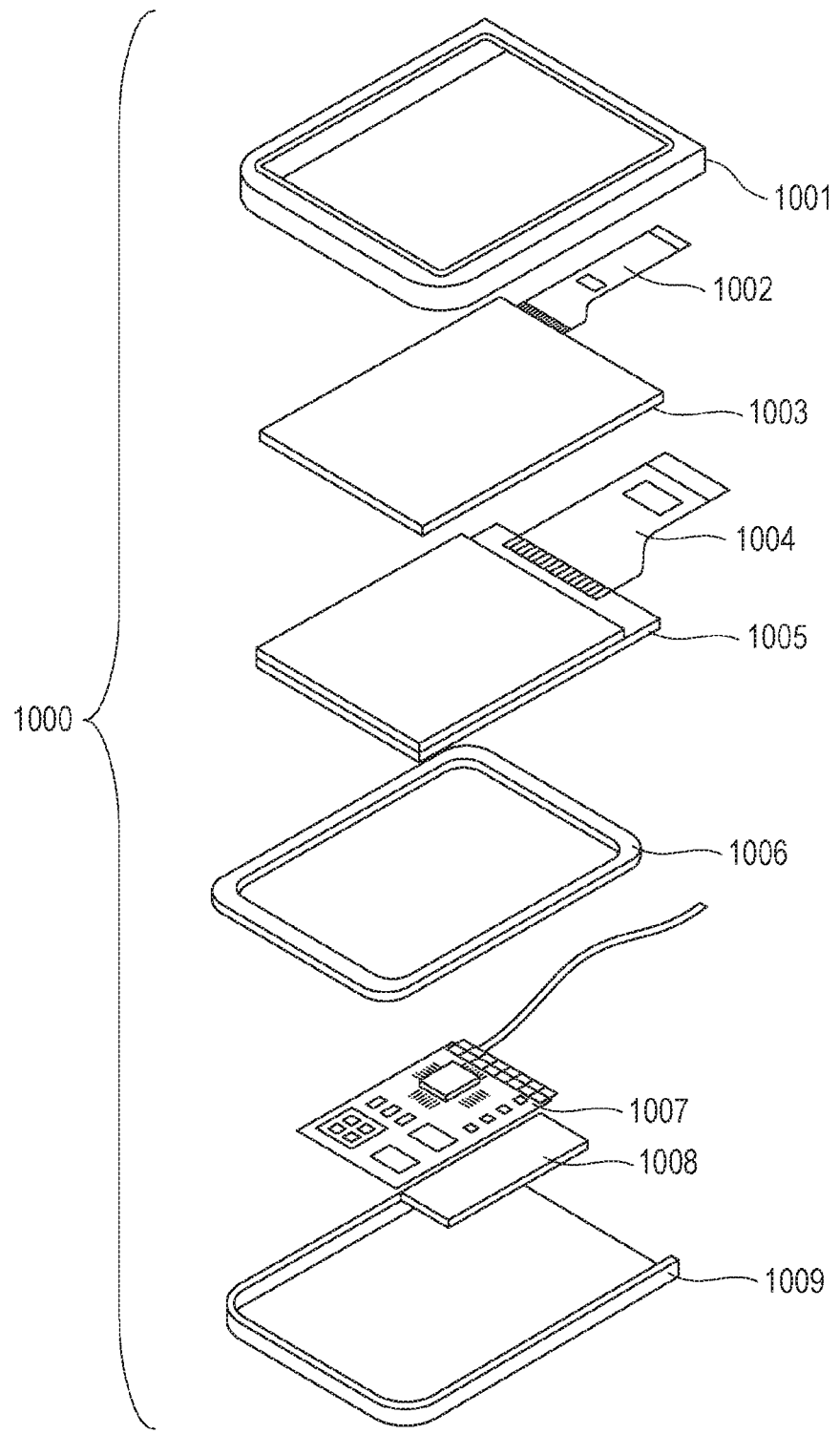
FIG. 4 is a schematic view illustrating an example of a display apparatus according to an embodiment of the present disclosure.

FIG. 4 schematically illustrates an example of a display apparatus according to an embodiment of the present disclosure. A display apparatus 1000 may include a touch panel 1003, a display panel 1005, a frame 1006, a circuit board 1007, and a battery 1008 between an upper cover 1001 and a lower cover 1009. Flexible printed circuits FPC 1002 and 1004 are connected to the touch panel 1003 and the display panel 1005, respectively. A transistor is printed on the circuit board 1007. The battery 1008 is not necessarily disposed if the display apparatus is not a mobile apparatus. Even if the display apparatus is a mobile apparatus, the battery 1008 is not necessarily disposed at this position.

The display apparatus according to an embodiment of the present disclosure may be used in a display unit of an image pickup apparatus that includes an optical unit including a plurality of lenses and an image pickup element configured to receive light that has passed through the optical unit. The image pickup apparatus may include a display unit configured to display information obtained by the image pickup element. The display unit may be a display unit exposed to the outside of the image pickup apparatus or a display unit disposed in a viewfinder. The image pickup apparatus may be a digital camera or a digital camcorder.

Figure 5A:
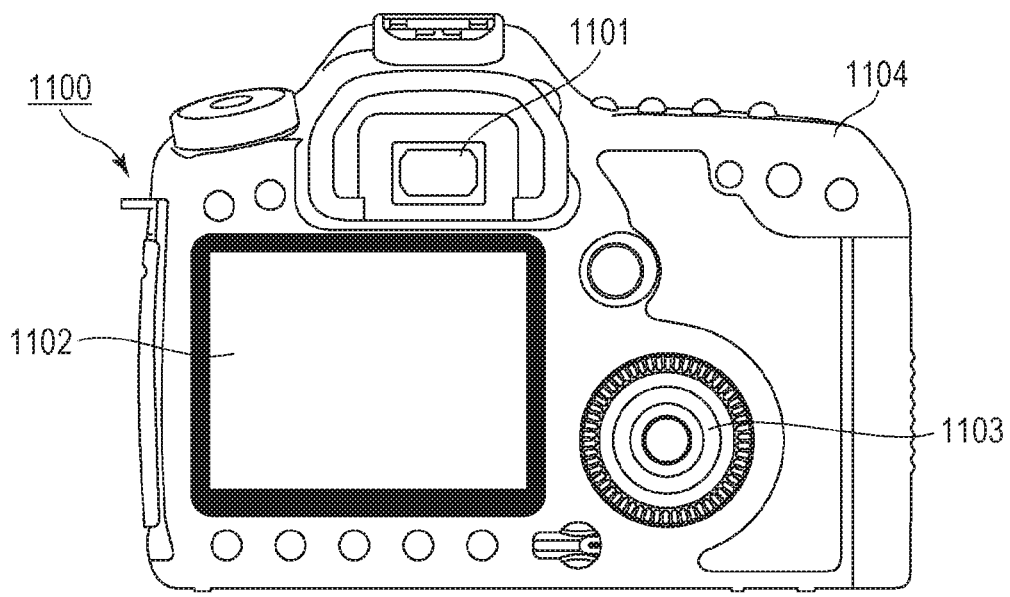
FIG. 5A is a schematic view illustrating an example of an image pickup apparatus according to an embodiment of the present disclosure.

FIG. 5A is a schematic view illustrating an example of an image pickup apparatus according to an embodiment of the present disclosure. An image pickup apparatus 1100 may include a viewfinder 1101, a rear display 1102, an operating unit 1103, and a housing 1104. The viewfinder 1101 may include the display apparatus according to an embodiment of the present disclosure. In this case, the display apparatus may display not only an image to be captured, but also environmental information, image capturing instructions, and the like. The environmental information may be, for example, the intensity of external light, the direction of external light, the moving speed of a subject, and the possibility that the subject is hidden by an object.

Since the timing appropriate for capturing an image is only a moment, the information is desirably displayed as quickly as possible. Therefore, the display apparatus including the organic light-emitting element according to an embodiment of the present disclosure can be used. This is because the organic light-emitting element has a high response speed. The display apparatus including the organic light-emitting element can be more suitably used than the apparatuses and liquid crystal display apparatuses that are required to have a high display speed.

The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

The display apparatus according to an embodiment of the present disclosure may include red, green, and blue color filters. The red, green, and blue color filters may be disposed in a delta arrangement.

The display apparatus according to an embodiment of the present disclosure may be used in a display unit of a mobile terminal. The display unit may have both a display function and an operational function. Examples of the mobile terminal include mobile phones such as smartphones, tablet computers, and head-mounted displays.

Figure 5B:
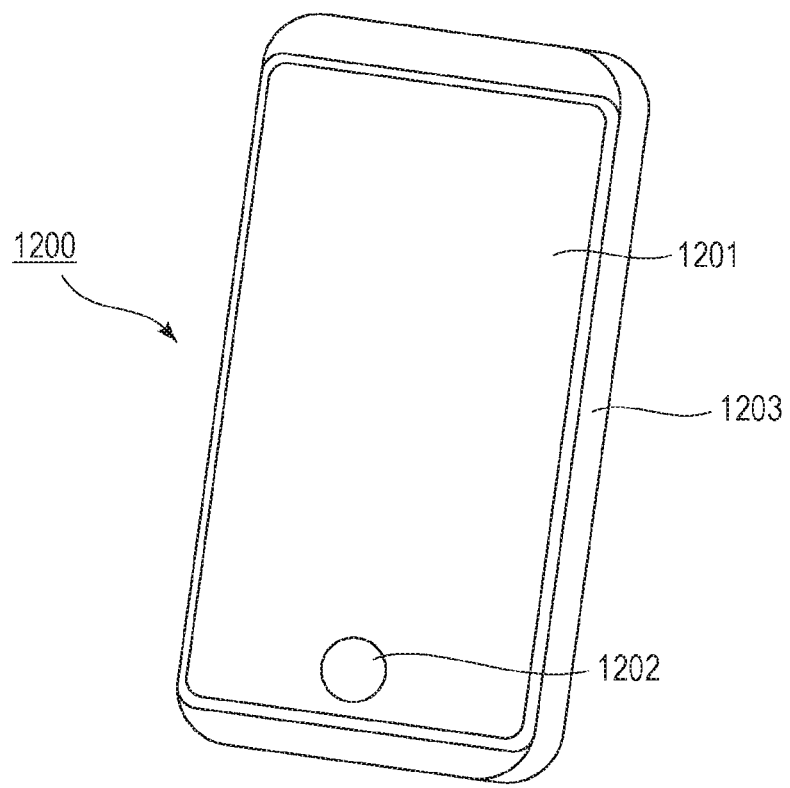
FIG. 5B is a schematic view illustrating an example of a mobile apparatus according to an embodiment of the present disclosure.

FIG. 5B is a schematic view illustrating an example of an electronic apparatus according to an embodiment of the present disclosure. An electronic apparatus 1200 includes a display unit 1201, an operating unit 1202, and a housing 1203. The housing 1203 may include a circuit, a printed board including the circuit, a battery, and a communication unit. The operating unit 1202 may be a button or a touch panel response unit. The operating unit may be a biometric authentication unit that releases a lock through recognition of fingerprints. An electronic apparatus including a communication unit may be referred to as a communication apparatus.

Figure 6A:
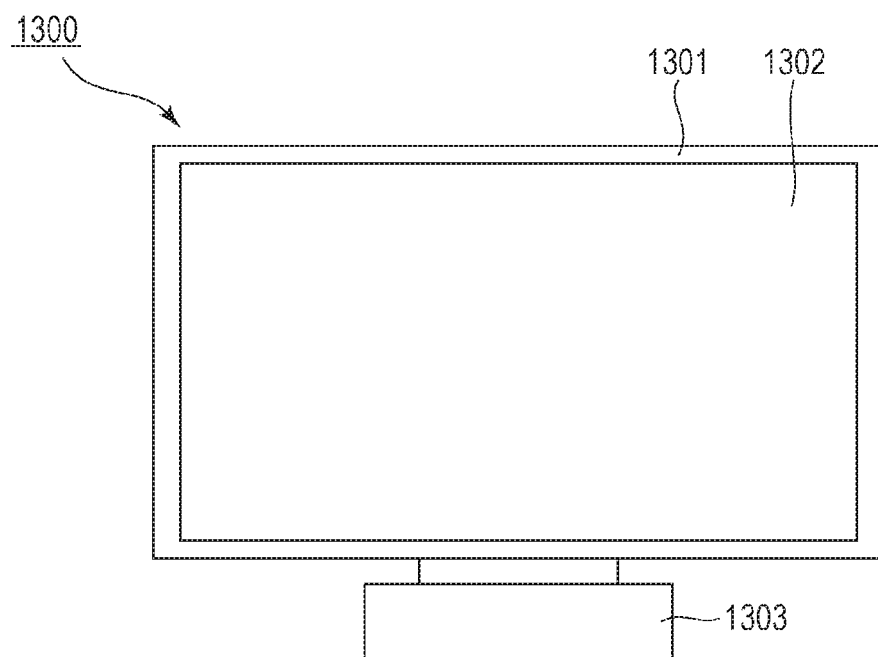
FIG. 6A is a schematic view illustrating an example of a display apparatus according to an embodiment of the present disclosure.
Figure 6B:
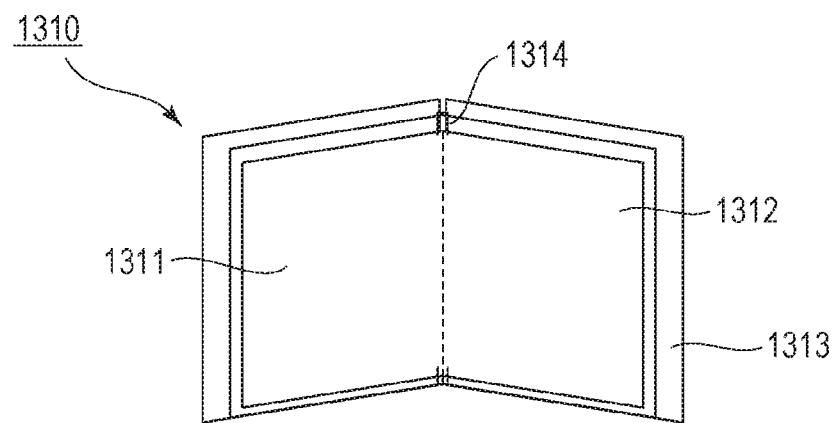
FIG. 6B is a schematic view illustrating an example of a foldable display apparatus.

FIGS. 6A and 6B are schematic views illustrating examples of display apparatuses according to embodiments of the present disclosure. FIG. 6A illustrates a display apparatus such as a television monitor or a PC monitor. A display apparatus 1300 includes a frame 1301 and a display unit 1302. The light-emitting device according to an embodiment of the present disclosure may be used in the display unit 1302.

The display apparatus 1300 includes a base 1303 that supports the frame 1301 and the display unit 1302. The form of the base 1303 is not limited to that in FIG. 6A. The lower side of the frame 1301 may also serve as a base.

The frame 1301 and the display unit 1302 may be curved. The radius of curvature may be 5000 mm or more and 6000 mm or less.

FIG. 6B is a schematic view illustrating another example of the display apparatus according to an embodiment of the present disclosure. A display apparatus 1310 in FIG. 6B is a so-called foldable display apparatus. The display apparatus 1310 includes a first display unit 1311, a second display unit 1312, a housing 1313, and a bending point 1314. The first display unit 1311 and the second display unit 1312 may include the light-emitting device according to an embodiment of the present disclosure. The first display unit 1311 and the second display unit 1312 may constitute a single seamless display apparatus. The first display unit 1311 and the second display unit 1312 can be divided by the bending point. The first display unit 1311 and the second display unit 1312 may display different images or a single image may be displayed in a combination of the first and second display units.

Figure 7A:
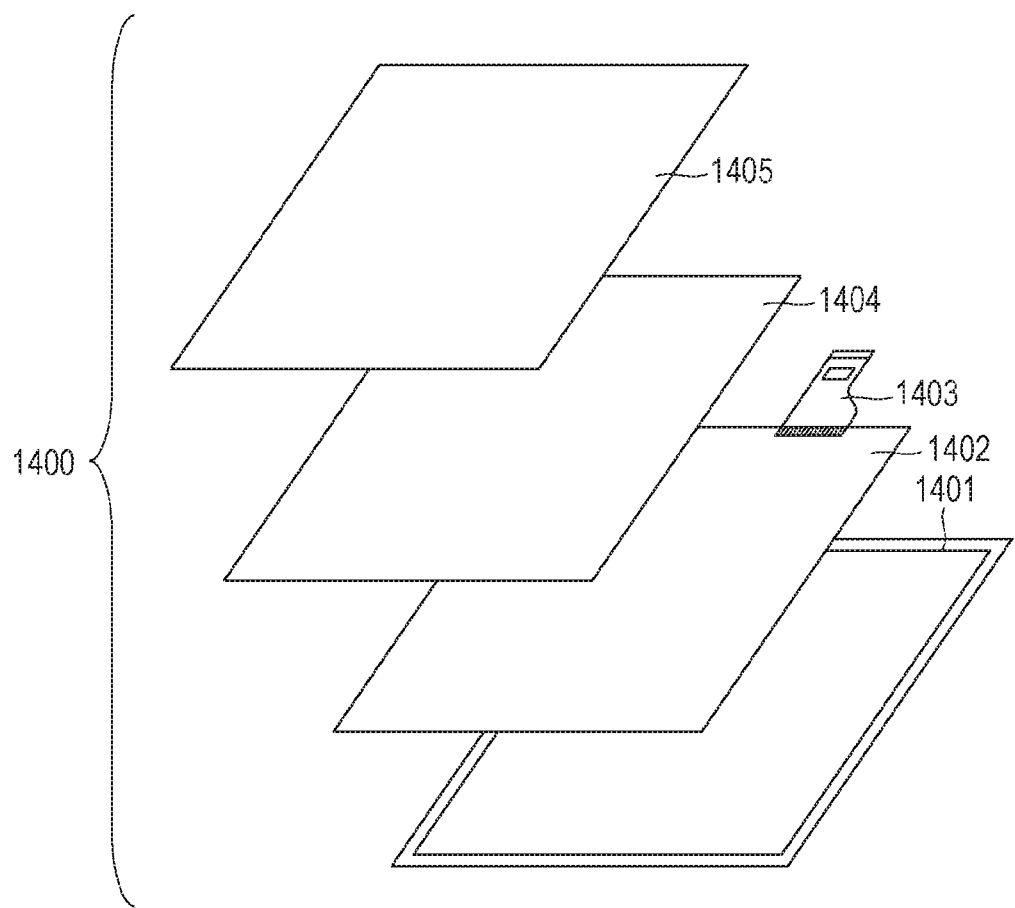
FIG. 7A is a schematic view illustrating an example of a lighting apparatus according to an embodiment of the present disclosure.

FIG. 7A is a schematic view illustrating an example of a lighting apparatus according to an embodiment of the present disclosure. A lighting apparatus 1400 may include a housing 1401, a light source 1402, a circuit board 1403, an optical film 1404, and a light diffusion unit 1405. The light source may include the organic light-emitting element according to an embodiment of the present disclosure. The optical film may be a film that improves the color rendering of the light source. The light diffusion unit used for lighting up or the like effectively diffuses light from the light source and allows the light to reach a wide area. The optical filter and the light diffusion unit may be disposed on the light-emitting side of the lighting apparatus. A cover may be optionally disposed on the outermost part.

The lighting apparatus is, for example, an apparatus that lights a room. The lighting apparatus may emit light of white, natural white, or any other color from blue to red. The lighting apparatus may include a light modulation circuit configured to modulate the light. The lighting apparatus may include the organic light-emitting element according to an embodiment of the present disclosure and a power supply circuit connected to the organic light-emitting element. The power supply circuit is a circuit that converts an alternating voltage to a direct voltage. The color "white" has a color temperature of 4200 K and the color "natural white" has a color temperature of 5000 K. The lighting apparatus may include a color filter.

The lighting apparatus according to an embodiment of the present disclosure may also include a heat dissipation unit. The heat dissipation unit dissipates heat in the apparatus to the outside and is formed of, for example, a metal having a high specific heat or a liquid silicon.

Figure 7B:
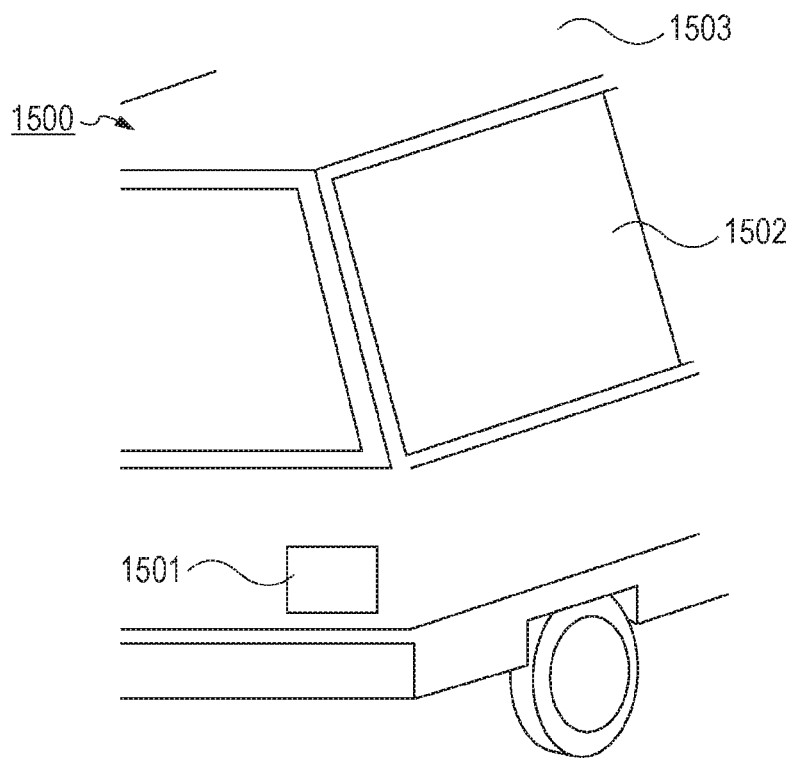
FIG. 7B is a schematic view illustrating an automobile that is an example of a moving object according to an embodiment of the present disclosure.

FIG. 7B is a schematic view illustrating an automobile that is an example of a moving object according to an embodiment of the present disclosure. The automobile includes a tail lamp that is an example of a lighting fixture. An automobile 1500 includes a tail lamp 1501, and the tail lamp may be lit through, for example, application of the brake.

The tail lamp 1501 may include the organic light-emitting element according to an embodiment of the present disclosure. The tail lamp may include a protective member that protects the organic light-emitting element. The protective member may be made of any material as long as the protective member has a relatively high strength and transparency. The protective member may be made of polycarbonate or the like. The polycarbonate may be mixed with, for example, a furandicarboxylic acid derivative or an acrylonitrile derivative.

The automobile 1500 may include a car body 1503 and windows 1502 attached to the car body 1503. The windows may be transparent displays as long as the windows are not a front or rear window of the automobile. The transparent display may include the organic light-emitting element according to an embodiment of the present disclosure. In this case, for example, the electrode included in the organic light-emitting element is formed of a transparent material.

The moving object according to an embodiment of the present disclosure may be, for example, a ship, an aircraft, or a drone. The moving object may include a body and a lighting fixture disposed on the body. The lighting fixture may emit light for allowing the position of the body to be recognized. The lighting fixture may include the organic light-emitting element according to an embodiment of the present disclosure.

In the organic light-emitting element according to an embodiment of the present disclosure, the emission luminance is controlled by a TFT that is an example of a switching element. When a plurality of such organic light-emitting elements are arranged in a plane, an image can be displayed using an emission luminance of each of the organic light-emitting elements. The switching element according to this embodiment is not limited to TFTs. The switching element may be a transistor formed of low-temperature polysilicon or an active matrix driver formed on a substrate such as a Si substrate. The phrase "on a substrate" may also refer to "on a substrate" or "in a substrate". This is selected depending on the resolution. For example, in the case of a size of 1 inch and a resolution of about QVGA, organic light-emitting elements may be disposed on a Si substrate. By driving the display apparatus including the organic light-emitting elements according to an embodiment of the present disclosure, an image having good image quality can be stably displayed for a long time.

EXAMPLES

Hereafter, the present disclosure will be described based on Examples, but is not limited to Examples.

Example 1

Synthesis of Exemplary Compound A2

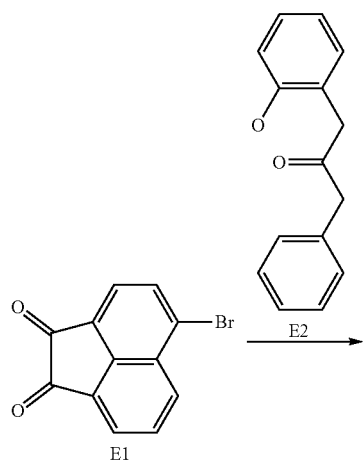

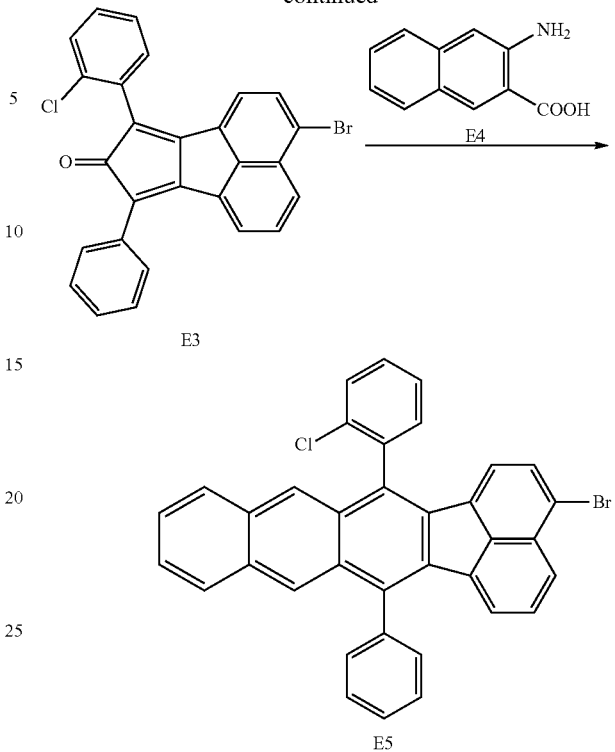

(1) Synthesis of Compound E3

The following reagents and solvent were charged into a 100 ml recovery flask.

Compound E1: 2.00 g (7.66 mmol)
Compound E2: 1.97 g (8.04 mmol)
Ethanol: 40 ml

Subsequently, a solution prepared by dissolving 556 mg (8.43 mmol) of 85% sodium hydroxide in 10 ml of ethanol was added dropwise thereto at room temperature. After the completion of the dropwise addition, the temperature was increased to 40° C. in a nitrogen stream, and stirring was performed at this temperature (40° C.) for 4 hours. After the completion of the reaction, water was added and the resulting product was filtered and washed by dispersion with water and methanol. Thus, 3.20 g of a dark green compound E3 (yield: 89%) was obtained.

(2) Synthesis of Compound E5

The following reagents and solvent were charged into a 100 ml recovery flask.

Compound E3: 3.00 g (6.39 mmol)
Compound E4: 1.44 g (7.67 mmol)
Isoamyl nitrite: 1.02 ml (7.67 mmol)
Toluene: 50 ml Subsequently, the reaction solution was heated to 105° C. in a nitrogen stream and stirred at this temperature (105° C.) for 2 hours. Furthermore, 480 mg (2.56 mmol) of the compound E4 and 0.34 ml (2.56 mmol) of the isoamyl nitrite were added thereto, and stirring was performed for 2 hours. After the completion of the reaction, the resulting product was extracted with toluene and water, then concentrated, purified by silica gel column chromatography (heptane: toluene=4:1), and then washed by dispersion with heptane/ethanol. Thus, 1.81 g of a yellow compound E5 (yield: 50%) was obtained.

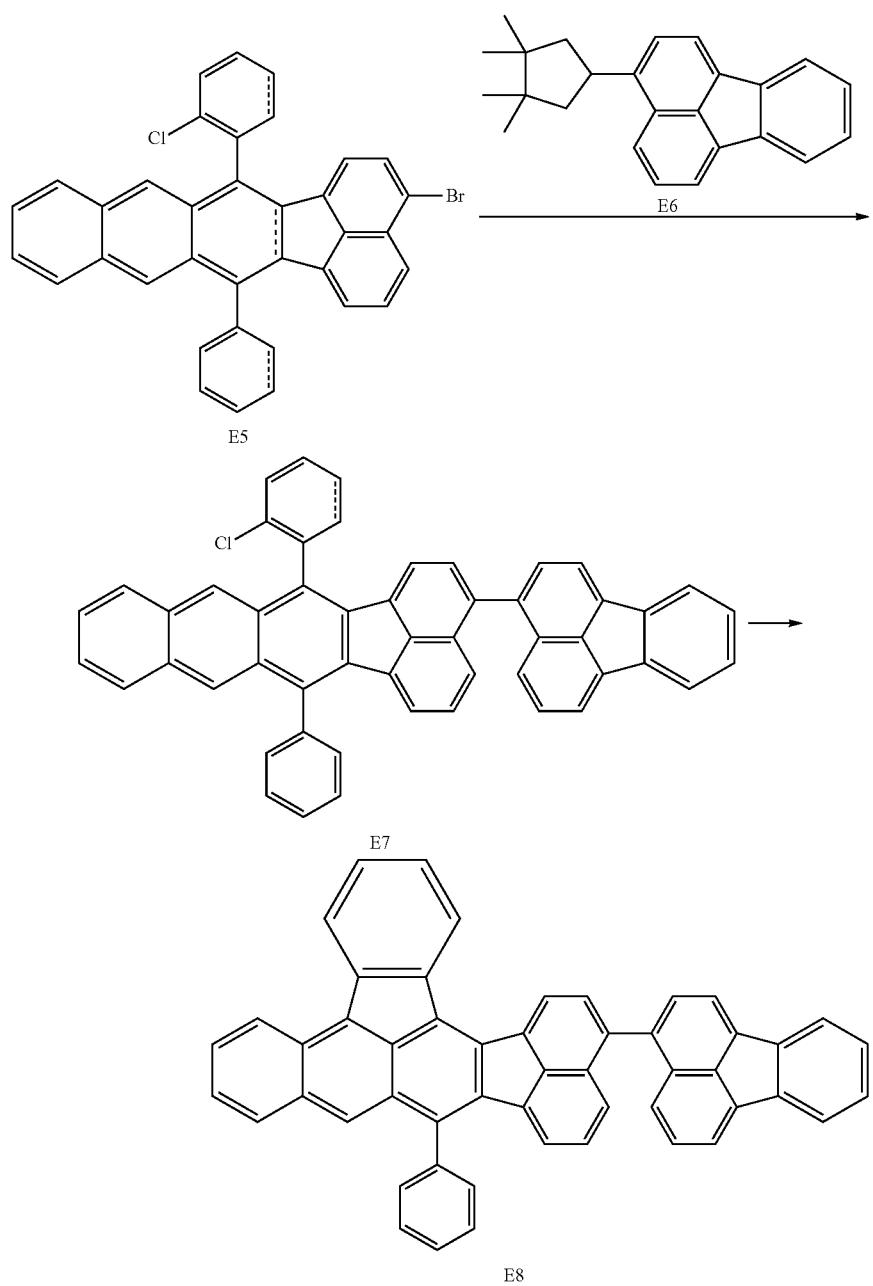

(3) Synthesis of Compound E7
The following reagents and solvents were charged into a 100 ml recovery flask.
Compound E5: 1.00 g (1.76 mmol)
Compound E6: 607 mg (1.85 mmol)
Pd(PPh$_3$)$_4$: 61 mg (0.053 mmol)
Cesium carbonate: 2.29 g (7.04 mmol)
Toluene: 18 ml
Ethanol: 9 ml
Water: 9 ml Subsequently, the reaction solution was heated to 90° C. in a nitrogen stream and stirred at this temperature (90° C.) for 4 hours. After the completion of the reaction, the resulting product was extracted with toluene and water, then concentrated, purified by silica gel column chromatography (heptane:chloroform=4:1), and then washed by dispersion with heptane/ethanol. Thus, 1.07 g of a yellow compound E8 (yield: 88%) was obtained.

(4) Synthesis of Compound E8
The following reagents and solvent were charged into a 50 ml recovery flask.
Compound E7: 1.00 g (1.45 mmol)
Pd(dba)$_2$: 173 mg (0.44 mmol)
P(Cy)$_3$ (tricyclohexylphosphine): 252 mg (0.90 mmol)
DBU (diazabicycloundecene): 0.87 ml (5.80 mmol)
DMAc: 25 ml Subsequently, the reaction solution was heated to 170° C. in a nitrogen stream and stirred at this temperature (170° C.) for 5 hours. After the completion of the reaction, methanol was added to precipitate a crystal. Then, the crystal was separated by filtration and sequentially washed by dispersion with water, methanol, ethanol, and heptane. Subsequently, the obtained yellow crystal was purified by silica gel column chromatography (heptane:chloroform=4:1) and then washed by dispersion with heptane/ethanol. Thus, 947 mg of a yellow compound E8 (yield: 78%) was obtained.

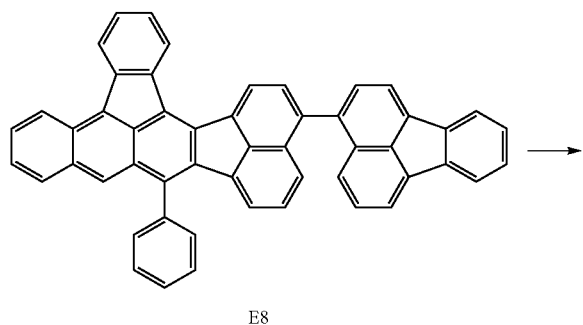

E8

(5) Synthesis of Exemplary Compound A2

The following reagents and solvent were charged into a 20 ml recovery flask.
Compound E8: 300 mg (0.460 mmol)
t-BuOK: 2.06 g (18.4 mmol)
DBU (diazabicycloundecene): 5.50 ml (36.8 mmol)
Diethylene glycol dimethyl ether: 18 ml Subsequently, the reaction solution was heated to 180° C. in a nitrogen stream and stirred at this temperature (180° C.) for 10 hours. After the completion of the reaction, water was added to precipitate a crystal. Then, the crystal was separated by filtration and sequentially washed by dispersion with water, methanol, ethanol, and heptane. Subsequently, the obtained deep purple solid was dissolved in chlorobenzene at 130° C., and alumina was added thereto to perform a heat adsorption process. The resulting product was hot-filtered, concentrated, and washed by dispersion with acetone/heptane. Thus, 251 mg of a deep purple exemplary compound A2 (yield: 84%) was obtained.

A toluene solution of the exemplary compound A2 in a concentration of $1\times10^{-5}$ mol/L was subjected to photoluminescence measurement at an excitation wavelength of 350 nm using an F-4500 manufactured by Hitachi, Ltd. The emission spectrum showed a peak having the maximum intensity at 623 nm.

The exemplary compound A2 was subjected to mass spectrometry using MALDI-TOF-MS (Autoflex LRF manufactured by Bruker).

MALDI-TOF-MS
Measured value: m/z=651, Calculated value: $C_{52}H_{26}$=651

Examples 2 to 16

Synthesis of Exemplary Compound

Exemplary compounds shown in Tables 4-1 and 4-2 below were synthesized in the same manner as in Example 1, except that the raw materials E1, E2, and E7 in Example 1 were changed to raw materials 1, 2, and 3. The exemplary compounds were subjected to mass spectrometry in the same manner as in Example 1 to determine the measured value m/z.

TABLE 4-1

| Example | Exemplary compound |
|---|---|
| 2 | A5 |

TABLE 4-1-continued
3 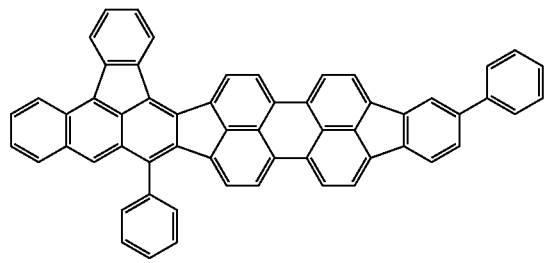
A6
4 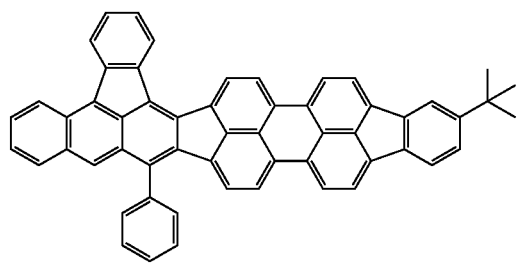
A10
5 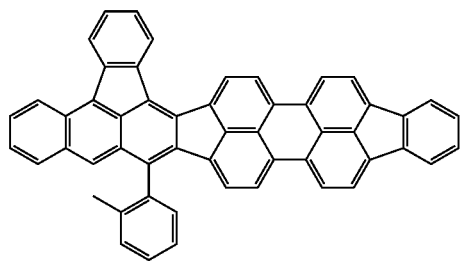
B1
6 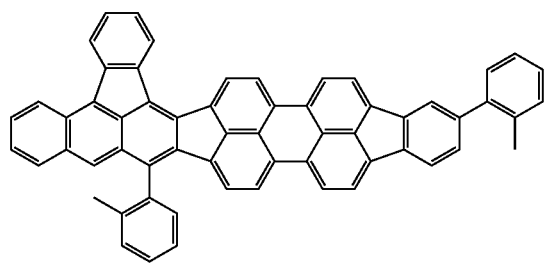
B3
7 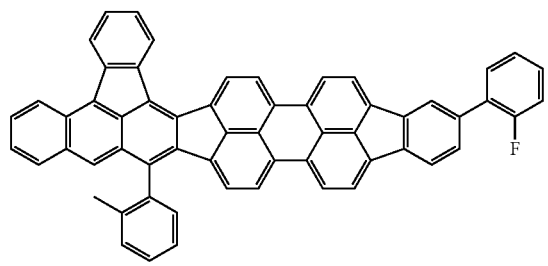
B11

TABLE 4-1-continued
| | |
|---|---|
| 8 | 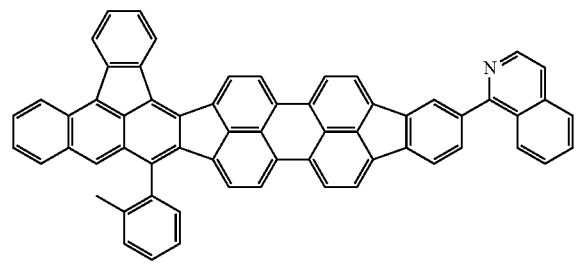B15 |
| 9 | B16 |
| 10 | C1 |
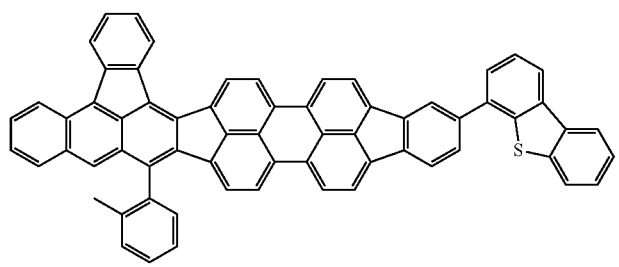
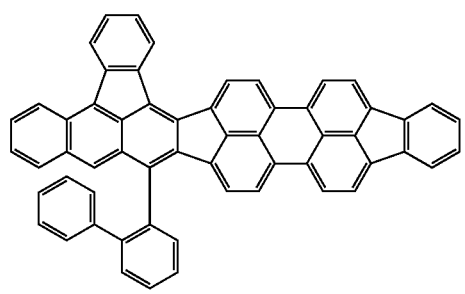
| Example | Raw material 1 | Raw material 2 | Raw material 3 | m/z |
|---|---|---|---|---|
| 2 | | | | 727 |
| 3 | | | | 727 |

TABLE 4-1-continued

| | | | | |
|---|---|---|---|---|
| 4 | 2-chlorophenyl-acetone with benzyl | 3-amino-2-naphthoic acid | pinacol boronate of tert-butyl-fluoranthene | 707 |
| 5 | 2-chlorophenyl-acetone with o-tolyl | 3-amino-2-naphthoic acid | pinacol boronate of fluoranthene | 665 |
| 6 | 2-chlorophenyl-acetone with o-tolyl | 3-amino-2-naphthoic acid | pinacol boronate of o-tolyl-fluoranthene | 755 |
| 7 | 2-chlorophenyl-acetone with o-tolyl | 3-amino-2-naphthoic acid | pinacol boronate of 2-fluorophenyl-fluoranthene | 759 |
| 8 | 2-chlorophenyl-acetone with o-tolyl | 3-amino-2-naphthoic acid | pinacol boronate of isoquinolinyl-fluoranthene | 792 |
| 9 | 2-chlorophenyl-acetone with o-tolyl | 3-amino-2-naphthoic acid | pinacol boronate of dibenzothiophenyl-fluoranthene | 847 |

TABLE 4-1-continued
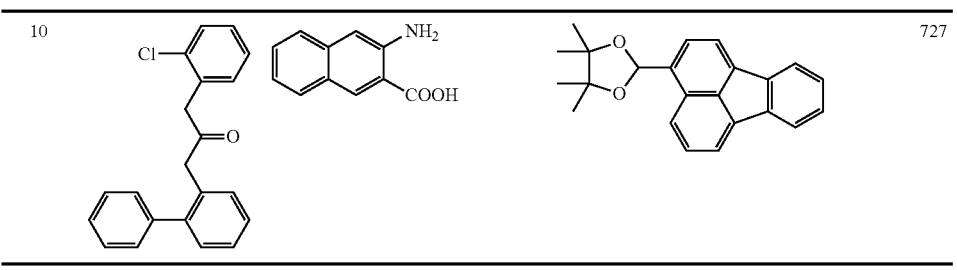
TABLE 4-2
| Example | Exemplary compound |
|---|---|
| 11 | |
| 12 | |
| 13 | |
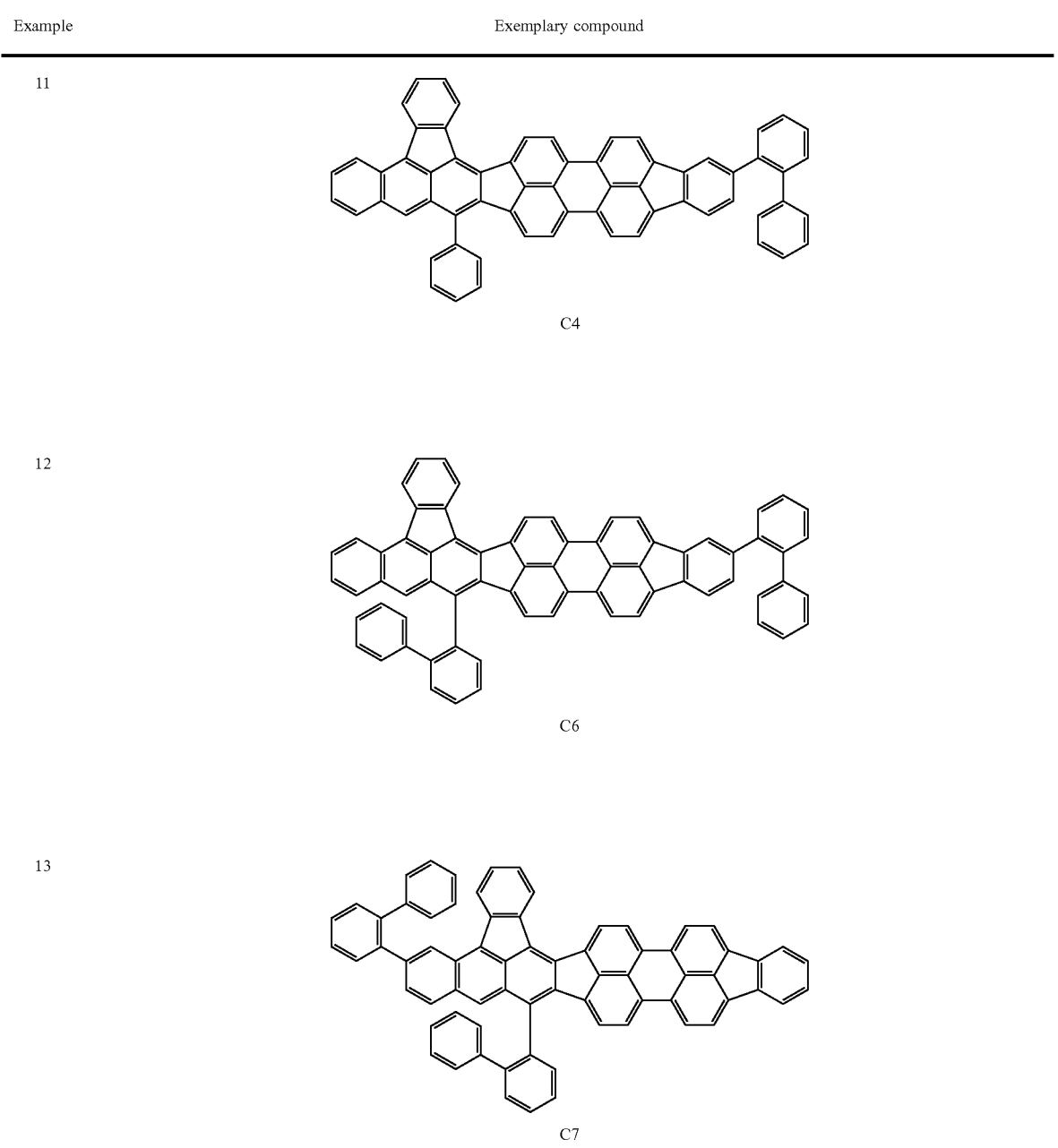

TABLE 4-2-continued
14
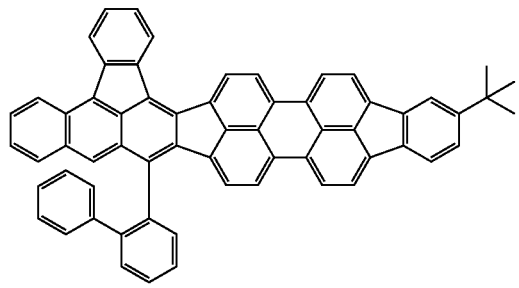
C12
15
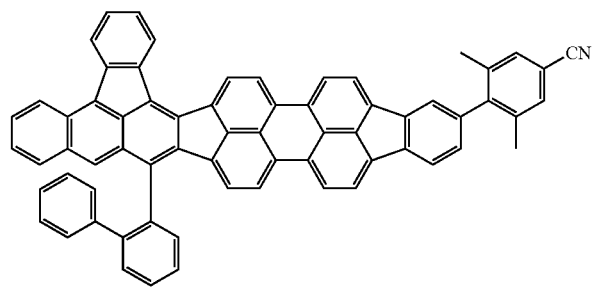
C16
16
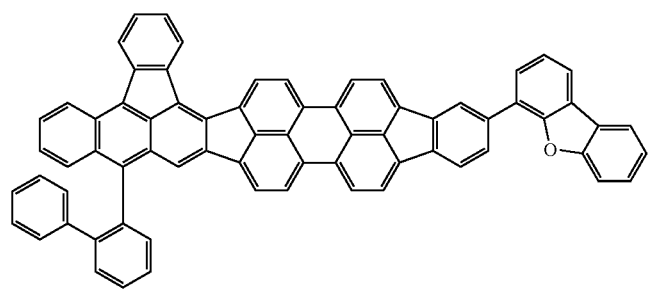
C19
| Example | Raw material 1 | Raw material 2 | Raw material 3 | m/z |
|---|---|---|---|---|
| 11 | (structure) | (structure) | (structure) | 803 |
| 12 | (structure) | (structure) | (structure) | 879 |

TABLE 4-2-continued

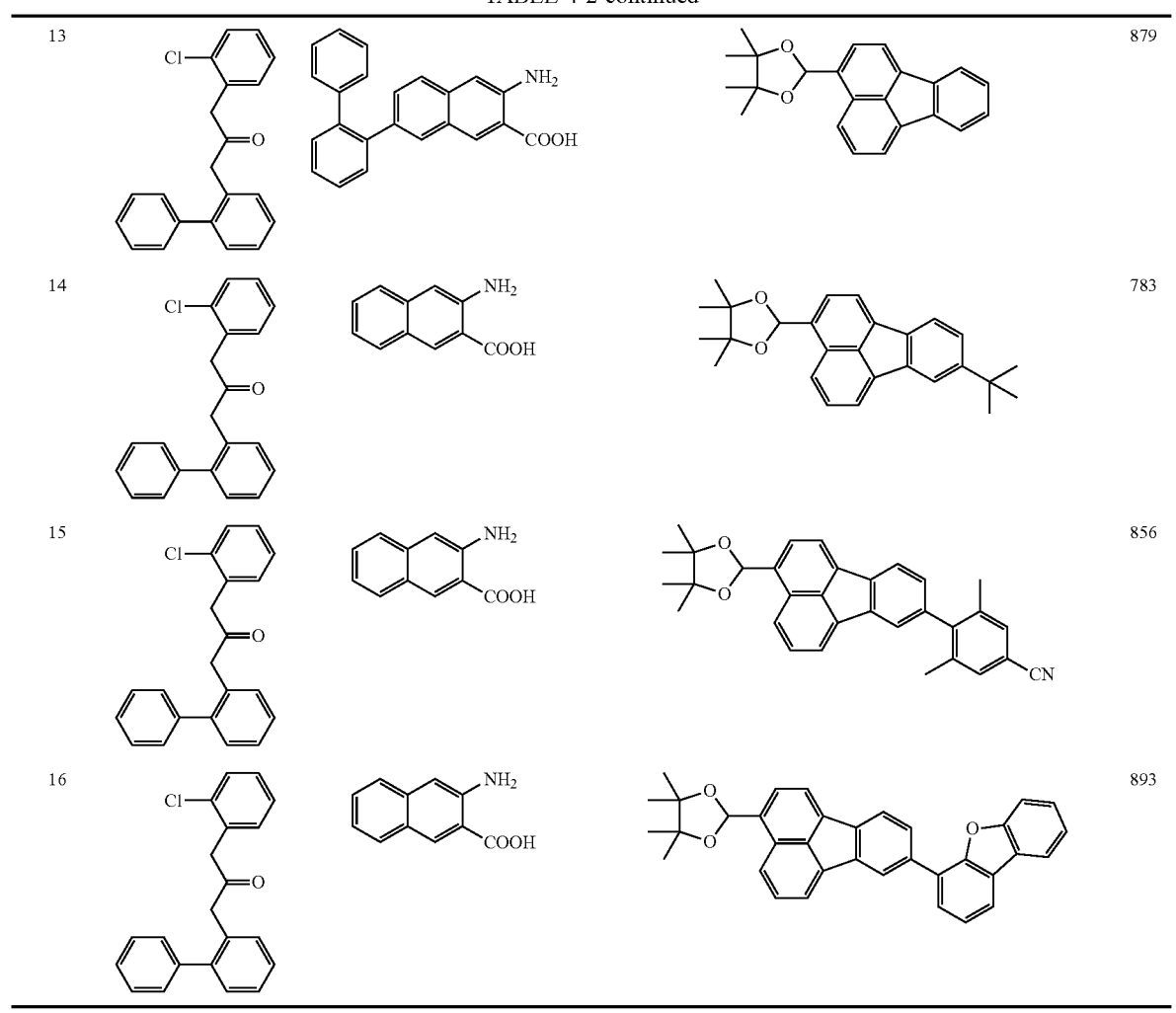

Example 17

In Example 17, as shown in Table 5, a bottom-emission organic EL element was produced in which an anode, a hole injection layer (HIL), a hole transport layer (HTL), an electron blocking layer (EBL), a light-emitting layer (EML), a hole blocking layer (HBL), an electron transport layer (ETL), an electron injection layer (EIL), and a cathode were sequentially formed on a substrate.

The light-emitting layer contains a host and a guest. The weight ratio of the host to the guest is host:guest=99.7:0.3.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process.

Subsequently, the organic EL layers and the electrode layers shown in Table 5 below were successively formed on the ITO substrate by performing vacuum vapor deposition through resistance heating in a vacuum chamber at 1.33×10 Pa. At this time, the electrode area of a counter electrode (metal electrode layer, cathode) was set to 3 mm$^2$.

TABLE 5

|  | Material |  | Thickness (nm) |
| --- | --- | --- | --- |
| Cathode | Al |  | 100 |
| Electron injection layer | LiF |  | 1 |
| Electron transport layer | ET5 |  | 20 |
| Hole blocking layer | ET17 |  | 20 |
| Light-emitting layer | Host | EM17 | 30 |
|  | Guest | A2 |  |
| Electron blocking layer | HT12 |  | 15 |
| Hole transport layer | HT3 |  | 30 |
| Hole injection layer | HT16 |  | 5 |
| Anode | ITO |  | 100 |

The characteristics of the obtained element were measured and evaluated. The light-emitting element had a maximum emission wavelength of 623 nm and a maximum external quantum efficiency (E.Q.E.) of 4.7%, and emitted red light with a chromaticity of (X, Y)=(0.68, 0.32). The current-voltage characteristics were measured with a microammeter 4140B manufactured by Hewlett-Packard Company. The emission luminance was measured with a BM7 manufactured by TOPCON Corporation. A continuous driving test at a current density of 100 mA/cm$^2$ was performed to measure a time taken when the luminance decrease reached 5%. The time was more than 500 hours.

Examples 18 to 28 and Comparative Example 1

Organic light-emitting elements were produced in the same manner as in Example 17, except that the compounds in Example 17 were appropriately changed to those in Table 6. The characteristics of the obtained elements were measured and evaluated in the same manner as in Example 17. Table 6 shows the measurement results.

TABLE 6

|  | HIL | HTL | EBL | EML Host | Guest | HBL | ETL | E.Q.E. [%] | Chromaticity coordinates of red (x, y) |
|---|---|---|---|---|---|---|---|---|---|
| Example 18 | HT16 | HT2 | HT11 | EM17 | A10 | ET12 | ET2 | 4.9 | (0.68, 0.32) |
| Example 19 | HT16 | HT2 | HT8 | EM16 | B1 | ET12 | ET3 | 4.8 | (0.67, 0.32) |
| Example 20 | HT16 | HT2 | HT12 | EM17 | B3 | ET10 | ET2 | 4.9 | (0.68, 0.32) |
| Example 21 | HT16 | HT1 | HT8 | EM16 | B3 | ET18 | ET3 | 5.0 | (0.68, 0.32) |
| Example 22 | HT16 | HT2 | HT12 | EM16 | B11 | ET12 | ET2 | 4.9 | (0.68, 0.32) |
| Example 23 | HT16 | HT2 | HT8 | EM17 | B16 | ET11 | ET2 | 4.9 | (0.68, 0.33) |
| Example 24 | HT16 | HT2 | HT8 | EM17 | C1 | ET18 | ET2 | 4.9 | (0.68, 0.32) |
| Example 25 | HT16 | HT1 | HT12 | EM16 | C6 | ET10 | ET2 | 5.0 | (0.69, 0.32) |
| Example 26 | HT16 | HT1 | HT12 | EM16 | C12 | ET10 | ET3 | 5.1 | (0.68, 0.32) |
| Example 27 | HT16 | HT2 | HT8 | EM17 | C6 | ET18 | ET3 | 5.0 | (0.69, 0.32) |
| Example 28 | HT17 | HT6 | HT8 | EM17 | C16 | ET18 | ET3 | 4.9 | (0.68, 0.32) |
| Comparative Example 1 | HT16 | HT3 | HT12 | EM17 | Comparative compound (2) | ET17 | ET5 | 4.7 | (0.66, 0.34) |

As is clear from Table 6, the chromaticity coordinates in Comparative Example 1 were (0.66, 0.34). The chromaticity coordinates of the red-light-emitting elements in which the organic compound represented by the formula (1) was used for a red-light-emitting layer were about (0.68, 0.32). The comparison between Examples and Comparative Example shows that the red light-emitting elements in Examples emit red light with a higher color purity than that in Comparative Example. The use of the light-emitting elements in Examples can achieve a color reproduction range wider than the color reproduction range of sRGB. The reason why the red light-emitting elements in Examples have a higher color purity is that the organic compound represented by the formula (1) emits red light having a longer wavelength.

Example 29

In Example 29, as shown in Table 7, a top-emission organic EL element was produced in which an anode, a hole injection layer (HIL), a hole transport layer (HTL), an electron blocking layer (EBL), a first light-emitting layer (1st EML), a second light-emitting layer (2nd EML), a hole blocking layer (HBL), an electron transport layer (ETL), an electron injection layer (EIL), and a cathode were sequentially formed on a substrate.

The first light-emitting layer contains a first host, a first guest, and a third guest. The first guest is a red-light-emitting material, and the third guest is a green-light-emitting material. The weight ratio in the first light-emitting layer is first host:first guest:third guest=96.7:0.3:3.0.

The second light-emitting layer contains a second host and a second guest. The second guest is a blue-light-emitting material. The weight ratio in the second light-emitting layer is second host:second guest=99.4:0.6.

The cathode contains Ag and Mg. The weight ratio of the components in the cathode is Ag:Mg=1:1.

Al and Ti were deposited on a glass substrate by a sputtering method and patterned by photolithography to form an anode. At this time, the electrode area of a counter electrode (metal electrode layer, cathode) was set to 3 mm$^2$.

Subsequently, the cleaned substrate on which the electrode had been formed and materials were placed in a vacuum evaporation system (manufactured by ULVAC, Inc.), and the system was evacuated to a pressure of 1.33× $10^{-4}$ Pa (1×$10^{-6}$ Torr) and then UV/ozone cleaning was performed. Subsequently, layers listed in Table 7 below were formed. Lastly, sealing was performed in a nitrogen atmosphere.

TABLE 7

|  | Material |  | Thickness (nm) |
|---|---|---|---|
| Cathode | Mg |  | 10 |
|  | Ag |  |  |
| Electron injection layer | LiF |  | 1 |
| Electron transport layer | ET2 |  | 30 |
| Hole blocking layer | ET12 |  | 70 |
| Second light-emitting layer | Second host | EM1 | 10 |
|  | Second guest | BD5 |  |
| First light-emitting layer | First host | EM1 | 10 |
|  | First guest | A10 |  |
|  | Third guest | GD8 |  |
| Electron blocking layer | HT7 |  | 15 |
| Hole transport layer | HT2 |  | 30 |
| Hole injection layer | HT16 |  | 5 |
| Anode | Ti |  | 6 |
|  | Al |  | 65 |

The characteristics of the obtained element were measured and evaluated. The obtained element exhibited good white-light emission. The chromaticity coordinates of red after transmission through an RGB color filter were estimated from the obtained white-light emission spectrum. The chromaticity coordinates of red in sRGB were (0.69, 0.32).

Examples 30 to 34 and Comparative Example 2

Organic light-emitting elements were produced in the same manner as in Example 29, except that the compounds were appropriately changed to those in Table 8. The characteristics of the obtained elements were measured and evaluated in the same manner as in Example 29. Table 8 shows the measurement results.

TABLE 8

| | 1st EML | | | 2nd EML | | Chromaticity |
|---|---|---|---|---|---|---|
| | First host | First guest | Third guest | Second host | Second guest | coordinates of red (x, y) |
| Example 30 | EM5 | B3 | GD8 | EM1 | BD4 | (0.69, 0.31) |
| Example 31 | EM1 | B11 | GD9 | EM5 | BD7 | (0.69, 0.31) |
| Example 32 | EM5 | C1 | GD4 | EM5 | BD5 | (0.70, 0.31) |
| Example 33 | EM1 | C6 | GD7 | EM1 | BD6 | (0.70, 0.30) |
| Example 34 | EM11 | C12 | GD4 | EM11 | BD6 | (0.70, 0.31) |
| Comparative Example 2 | EM1 | Comparative compound 1 | GD4 | EM1 | BD6 | (0.68, 0.33) |

As is clear from Table 7, the chromaticity coordinates of red in Comparative Example 2 are (0.68, 0.33). The chromaticity coordinates of red of the white-light-emitting elements in which the organic compound represented by the formula (1) is used for a red-light-emitting layer are about (0.70, 0.30). The comparison between Examples and Comparative Example shows that the white-light-emitting elements in Examples have a higher red color purity than that in Comparative Example. The use of the light-emitting elements in Examples can achieve a color reproduction range wider than the color reproduction range of sRGB. The reason why the red-light-emitting elements in Examples have a higher color purity is that the organic compound represented by the formula (1) emits red light having a longer wavelength.

According to the present disclosure, an organic compound whose basic skeleton itself can emit red light having a longer wavelength can be provided.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-177521, filed Sep. 21, 2018, which is hereby incorporated by reference herein in its entirety.

What is claimed is:

1. An organic compound represented by formula (1) below,

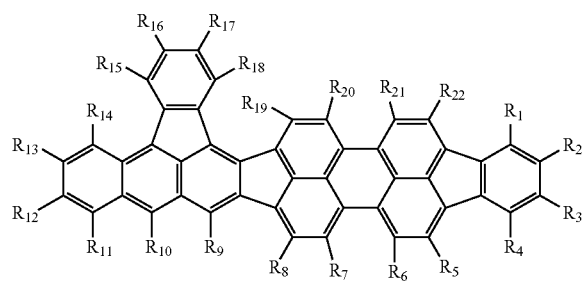

(1)

wherein each of $R_1$ to $R_{22}$ is independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group.

2. The organic compound according to claim 1, wherein at least one of $R_9$ and $R_{10}$ in the formula (1) is the substituted or unsubstituted aryl group.

3. The organic compound according to claim 2, wherein the substituted or unsubstituted aryl group is a phenyl group having a substituent at an ortho position thereof.

4. The organic compound according to claim 3, wherein the substituent introduced at an ortho position of the phenyl group is selected from the group consisting of a halogen atom, a substituted or unsubstituted alkyl group, a substituted or unsubstituted aryl group, a substituted or unsubstituted heterocyclic group, and a cyano group.

5. The organic compound according to claim 3, wherein the substituent introduced at an ortho position of the phenyl group is selected from the group consisting of a halogen atom, an alkyl group having 1 to 10 carbon atoms, and an aryl group having 6 to 18 carbon atoms.

6. The organic compound according to claim 3, wherein the substituent introduced at an ortho position of the phenyl group is selected from the group consisting of a fluorine atom, a methyl group, an isopropyl group, a tert-butyl group, and a phenyl group.

7. An organic light-emitting element comprising:
an anode;
a cathode; and
an organic compound layer disposed between the anode and the cathode,
wherein the organic compound layer contains the organic compound according to claim 1.

8. The organic light-emitting element according to claim 7, wherein the organic compound layer includes at least one light-emitting layer.

9. The organic light-emitting element according to claim 8,
wherein the organic compound layer further includes another light-emitting layer different from the light-emitting layer, and
the other light-emitting layer emits light having a color different from a color of light emitted from the light-emitting layer.

10. The organic light-emitting element according to claim 7, wherein the organic light-emitting element emits white light.

11. A display apparatus comprising a plurality of pixels, wherein at least one of the plurality of pixels includes the organic light-emitting element according to claim 7 and a transistor connected to the organic light-emitting element.

12. The display apparatus according to claim 11, comprising a color filter having an RGB delta arrangement on a light-emitting side of each of the pixels.

13. An image pickup apparatus comprising:
an optical unit including a plurality of lenses;
an image pickup element that receives light which has passed through the optical unit; and
a display unit that displays an image,
wherein the display unit displays an image captured by the image pickup element, and
the display unit includes the organic light-emitting element according to claim 7.

14. An electronic apparatus comprising:
a display unit including the organic light-emitting element according to claim 7;
a housing on which the display unit is disposed; and
a communication unit that is disposed on the housing and communicates with an outside.

15. A lighting apparatus comprising:
a light source including the organic light-emitting element according to claim 7; and
a light diffusion unit that diffuses light emitted from the light source or an optical film that transmits light emitted from the light source.

16. A moving object comprising:
a body; and
a lighting fixture disposed on the body,
wherein the lighting fixture includes the organic light-emitting element according to claim 7.

* * * * *